(12) United States Patent
Minbiole et al.

(10) Patent No.: US 8,980,925 B2
(45) Date of Patent: Mar. 17, 2015

(54) ANTIMICROBIAL AMPHIPHILES AND METHODS FOR THEIR USE

(75) Inventors: Kevin P. Minbiole, Media, PA (US); Kevin L. Caran, Harrisonburg, VA (US); Kyle N. Seifert, Harrisonburg, VA (US)

(73) Assignee: James Madison Innovations, Inc., Harrisonburg, VA (US)

( * ) Notice: Subject to any disclaimer, the term of this patent is extended or adjusted under 35 U.S.C. 154(b) by 0 days.

(21) Appl. No.: 13/879,930

(22) PCT Filed: Oct. 20, 2011

(86) PCT No.: PCT/US2011/057036
§ 371 (c)(1),
(2), (4) Date: Jun. 25, 2013

(87) PCT Pub. No.: WO2012/054695
PCT Pub. Date: Apr. 26, 2012

(65) Prior Publication Data
US 2014/0148487 A1    May 29, 2014

Related U.S. Application Data

(60) Provisional application No. 61/394,938, filed on Oct. 20, 2010.

(51) Int. Cl.
| | | |
|---|---|---|
| A61K 31/444 | (2006.01) | |
| C07D 213/04 | (2006.01) | |
| A01N 33/12 | (2006.01) | |
| A01N 43/40 | (2006.01) | |
| C07C 217/58 | (2006.01) | |
| C07D 213/02 | (2006.01) | |
| C07D 401/10 | (2006.01) | |
| C07D 401/14 | (2006.01) | |
| A61K 31/4425 | (2006.01) | |

(52) U.S. Cl.
CPC ............ *C07D 213/04* (2013.01); *A01N 33/12* (2013.01); *A01N 43/40* (2013.01); *C07C 217/58* (2013.01); *C07D 213/02* (2013.01); *C07D 401/10* (2013.01); *C07D 401/14* (2013.01); *A61K 31/4425* (2013.01)
USPC ............................................................... 514/332

(58) Field of Classification Search
None
See application file for complete search history.

(56) References Cited

U.S. PATENT DOCUMENTS 6,616,922 B2    9/2003    Taylor et al.

FOREIGN PATENT DOCUMENTS

| WO | WO 92/13048 | 8/1992 |
| WO | WO 2012/054695 | 4/2012 |

OTHER PUBLICATIONS

K.Z. Roszak et al. / Journal of Colloid and Interface Science 331 (2009) 560-564.*
Lee et al., "Soluble Electroluminescent Poly(phenylene vinylene)s with Balanced Electron and Hole Injections", J. Am. Chem. Soc., 2001, 123, 2296-2307.
Pernak et al., "Synthesis and Anti-Microbial Activities of Choline-like Quaternary Ammonium Chlorides", European Journal of Medicinal Chemistry, Sep. 2003, 38:1035-1042.
Roszak, et al., "Biscationic Bicephalic (Double-Headed) Amphiphiles with an Aromatic Spacer and a Single Hydrophobic Tail", J. Colloid Interface Sci., 2009, 331, 560-564.

* cited by examiner

*Primary Examiner* — Soren Harward
*Assistant Examiner* — Jeanmarie Calvillo
(74) *Attorney, Agent, or Firm* — Baker & Hostetler LLP

(57) ABSTRACT

The present invention is directed to compositions useful for antimicrobial applications. These compositions comprise amphiphilic compounds.

12 Claims, 2 Drawing Sheets

ANTIMICROBIAL AMPHIPHILES AND METHODS FOR THEIR USE

CROSS-REFERENCE TO RELATED APPLICATIONS

This application is the National Stage of International Application No. PCT/US2011/057036, filed Oct. 20, 2011, which claims the benefit of U.S. Provisional Application No. 61/394,938, filed Oct. 20, 2010, the disclosures of which are incorporated herein by reference in their entireties.

TECHNICAL FIELD

The present invention is directed to compositions useful for antimicrobial applications. These compositions comprise amphiphilic compounds.

BACKGROUND

Antibiotic resistance, particularly in human pathogens such as methicillin-resistant *Stapyhlococcus aureus* (MRSA), *Clostridium difficile*, vancomycin-resistant enterococci, and *Mycobacterium tuberculosis*, has increased dramatically in the last 20 years, which has threatened the ability to treat hospital- and community-acquired infections. Recently, widespread resistance to antibacterial compounds such as triclosan has also been observed, necessitating new antimicrobial compounds, particularly novel antibiotics and antiseptics. In addition to developing new antimicrobials by modifying existing drugs, antimicrobials with novel structures must also be developed, particularly compounds that will be difficult for organisms to inactivate or to resist via mutation. Compounds that present a unique strategy of activity are of premium importance.

Thus, new compounds having anti-microbial properties are needed.

SUMMARY

The present invention is directed to pharmaceutical compositions comprising at least one compound of formula I:

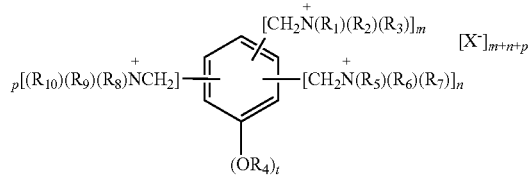

wherein $R_1$, $R_2$, $R_3$, $R_5$, $R_6$, $R_7$, $R_8$, $R_9$, and $R_{10}$ are each independently $C_{1-18}$alkyl or $R_1$, $R_2$, and $R_3$, and/or $R_5$, $R_6$, and $R_7$, and/or $R_8$, $R_9$, and $R_{10}$, together with the nitrogen atom to which they are attached, form a pyridinium or substituted pyridinium; m is 1; n is 0 or 1; p is 0 or 1; t is 0 or 1; $R_4$ is $C_{8-22}$alkyl; and X is halogen or tartrate; and a pharmaceutically acceptable carrier or diluent. Methods of inhibiting bacterial growth using pharmaceutical compositions and compounds of the invention are also described.

DETAILED DESCRIPTION OF ILLUSTRATIVE EMBODIMENTS

Figure 1A:
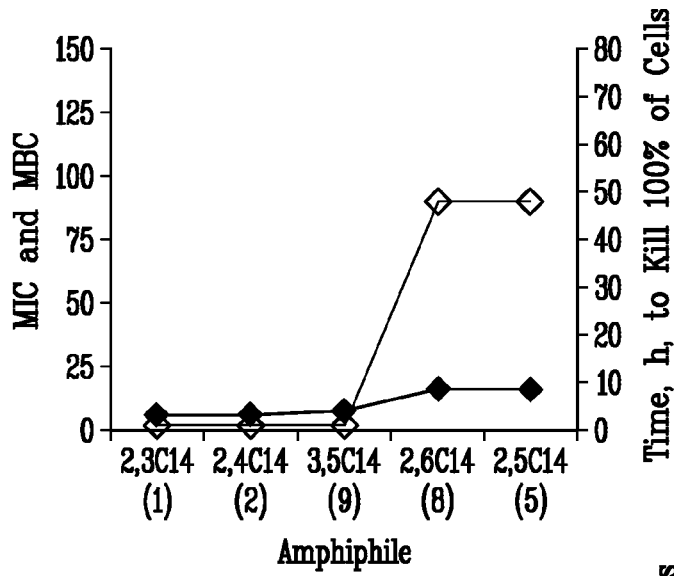
FIG. 1. Depicts antimicrobial activity of preferred embodiments of the invention against. (A) *S. aureus*, (B) *E. faecalis*, and (C) *E. coli*. Filled symbols (♦, ■, ●) indicate the MIC and MBC for each organism, while open symbols of the same shape (◊, □, ○) indicate the time necessary to kill 100% of the organism. *=time necessary to kill was >72 h.
Figure 1B:
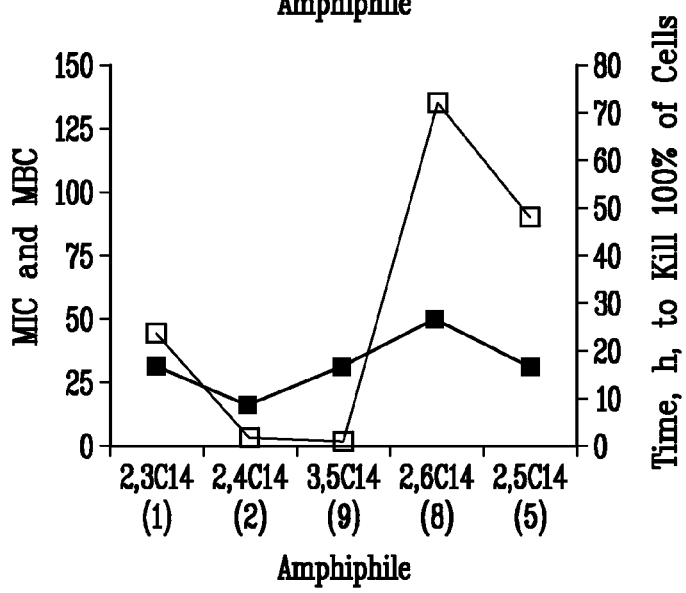
Figure 1C:
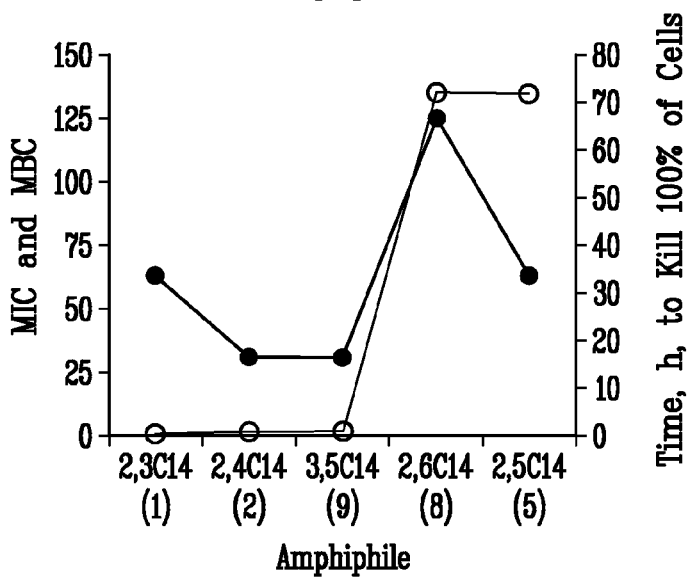
Figure 2A:
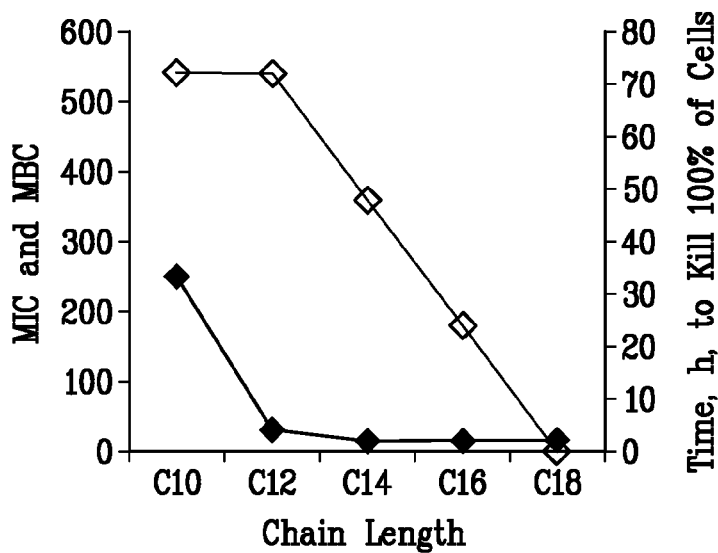
FIG. 2. Depicts antimicrobial activity of preferred embodiments of the invention against. (A) *S. aureus*, (B) *E. faecalis*, and (C) *E. coli*. Filled symbols (♦, ■, ●) indicate the MIC and MBC for each organism, while open symbols of the same shape (◊, □, ○) indicate the time necessary to kill 100% of the organism. *=time necessary to kill was >72 h. †=MIC values>500 μM.
Figure 2B:
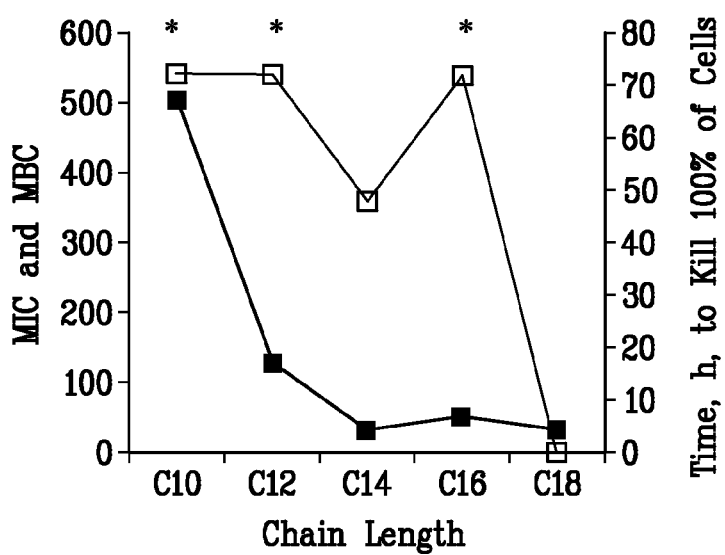
Figure 2C:
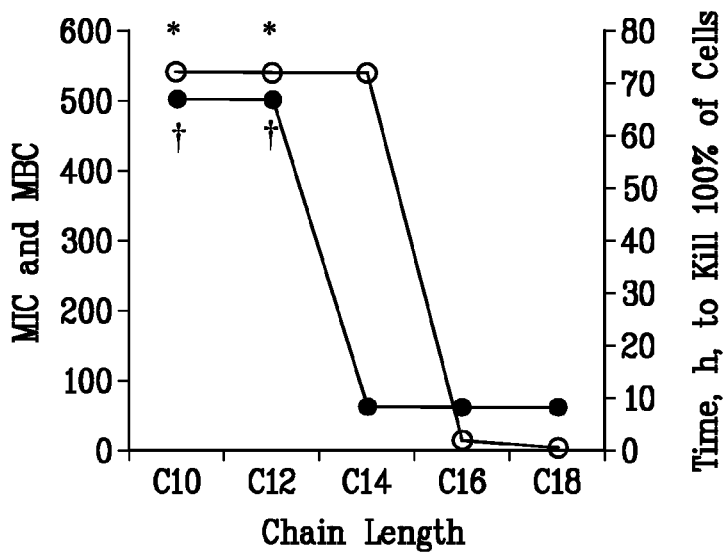

Compounds demonstrating anti-bacterial properties have been developed. These compounds are useful alone or in pharmaceutical compositions for the inhibition of bacterial growth.

The pharmaceutical compositions of the invention comprise at least one compound of formula I:

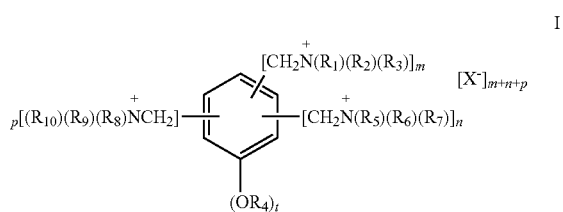

wherein
 $R_1$, $R_2$, $R_3$, $R_5$, $R_6$, $R_7$, $R_8$, $R_9$, and $R_{10}$ are each independently $C_{1-18}$alkyl or $R_1$, $R_2$, and $R_3$, and/or $R_5$, $R_6$, and $R_7$, and/or $R_8$, $R_9$, and $R_{10}$, together with the nitrogen atom to which they are attached, form a pyridinium or substituted pyridinium;
 m is 1;
 n is 0 or 1;
 p is 0 or 1;
 t is 0 or 1;
 $R_4$ is $C_{8-22}$alkyl; and
 X is halogen or tartrate;
 and a pharmaceutically acceptable carrier or diluent.

Certain embodiments of the invention include pharmaceutical compositions wherein m is 1; n is 0; p is 0; and t is 1. In such embodiments, it is preferred that each of $R_1$, $R_2$, and $R_3$ is independently $C_{1-3}$alkyl. More preferably, each of $R_1$, $R_2$, and $R_3$ is methyl. In such embodiments, preferred compounds of formula I have the following structure:

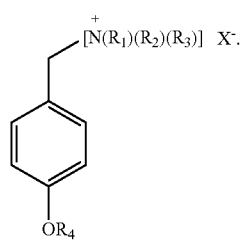

Other preferred embodiments of the invention include pharmaceutical compositions wherein m is 1; n is 1; p is 0;

and t is 1. In such embodiments, the compound of formula I preferably has one of the following structures:

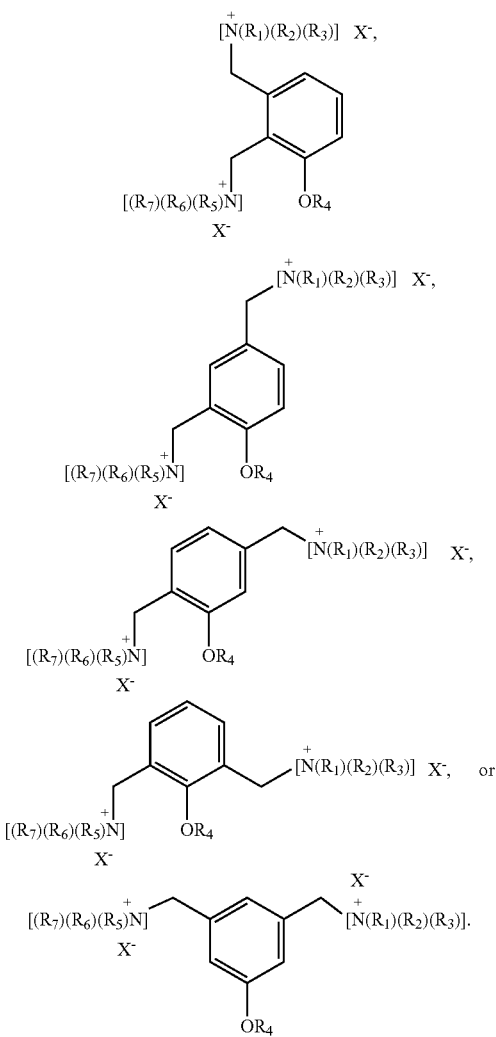

In such embodiments wherein m is 1; n is 1; p is 0; and t is 1, it is preferred that each of $R_1$, $R_2$, $R_3$, $R_5$, $R_6$, and $R_7$ are independently $C_{1-3}$alkyl. More preferred are embodiments wherein each of $R_1$, $R_2$, $R_3$, $R_5$, $R_6$, and $R_7$ is methyl.

In other embodiments, $R_1$, $R_2$, and $R_3$ and $R_5$, $R_6$, and $R_7$, together with the nitrogen atom to which they are attached, form a pyridinium. Of these embodiments, preferred compounds of formula I for use in pharmaceutical compositions of the invention include:

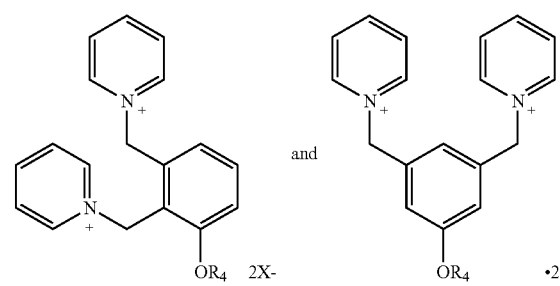

Other preferred embodiments include those wherein $R_1$, $R_2$, and $R_3$ and $R_5$, $R_6$, and $R_7$, together with the nitrogen atom to which they are attached, form a pyridyl-substituted pyridinium.

In other embodiments of the invention, $R_1$, $R_2$, and $R_3$ are each independently $C_{1-3}$alkyl and $R_5$, $R_6$, and $R_7$, together with the nitrogen atom to which they are attached, form a pyridinium or substituted pyridinium.

All of the foregoing embodiments of the invention include an $R_4$ moiety. For all such embodiments, $R_4$ is preferably —$C_{10}H_{21}$. Also preferred are embodiments where $R_4$ is —$C_{12}H_{25}$. Other preferred embodiments include those wherein $R_4$ is —$C_{14}H_{29}$. Particularly preferred are embodiments wherein $R_4$ is —$C_{16}H_{33}$. Additional embodiments include those wherein $R_4$ is —$C_{18}H_{37}$.

Preferred compounds of the invention for use in pharmaceutical compositions of the invention include:

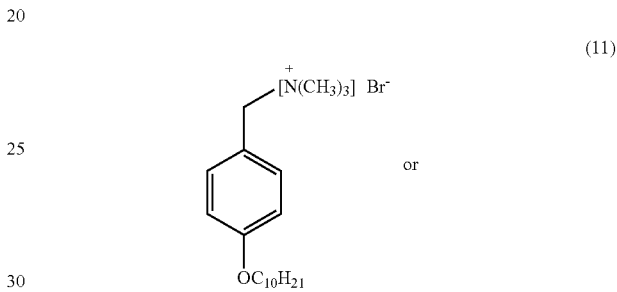

(11)

or

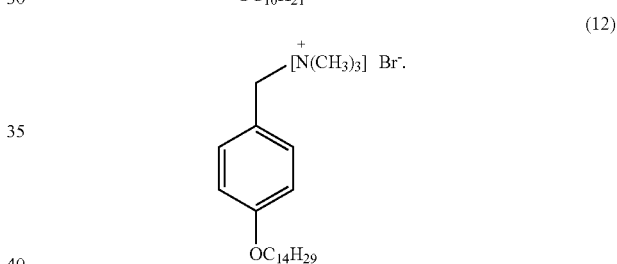

(12)

Other preferred compounds of formula I for use in pharmaceutical compositions of the invention include those selected from the following Table 1:

TABLE 1

| | |
|---|---|
| ![structure] | 4-[CH₂NH(CH₃)₃][Br⁻]<br>3,5-[CH₂N(CH₃)₃][Br⁻]<br>positions 1(OR₄), 2, 6 |

| Comp. No. | Substitution | $R_4$ |
|---|---|---|
| 1 | 2, 3 | —$C_{14}H_{29}$ |
| 2 | 2, 4 | —$C_{14}H_{29}$ |
| 3 | 2, 5 | —$C_{10}H_{21}$ |
| 4 | 2, 5 | —$C_{12}H_{25}$ |
| 5 | 2, 5 | —$C_{14}H_{29}$ |
| 6 | 2, 5 | —$C_{16}H_{33}$ |
| 7 | 2, 5 | —$C_{18}H_{37}$ |
| 8 | 2, 6 | —$C_{14}H_{29}$ |
| 9 | 3, 5 | —$C_{14}H_{29}$ |
| 10 | 3, 5 | —$C_{16}H_{33}$ |

Additionally preferred compounds of formula I for use in pharmaceutical compositions of the invention include those selected from the following Table 2:

TABLE 2

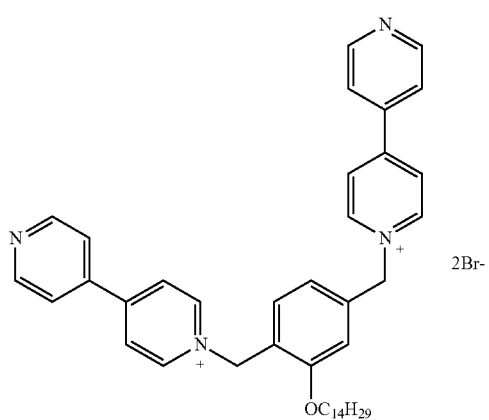

| Comp. No. | Substitution | R$_4$ |
|---|---|---|
| 15 | 2, 3 | —C$_{14}$H$_{29}$ |
| 40 | 3, 5 | —C$_{14}$H$_{29}$ |
| 16 | 3, 5 | —C$_{16}$H$_{33}$ |

A preferred compound of formula I for use in pharmaceutical compositions of the invention is:

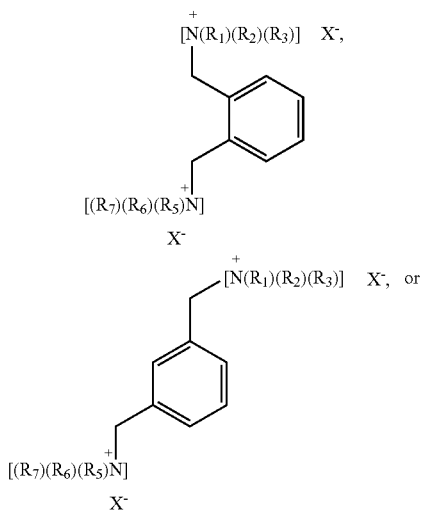

(41)

Also within the scope of the invention are pharmaceutical compositions of the invention that include compounds of formula I wherein m is 1; n is 1; p is 0; and t is 0. In such embodiments, it is preferred that the compound of formula I is one of

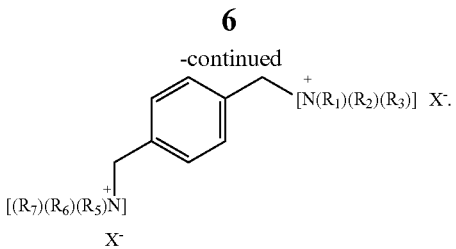

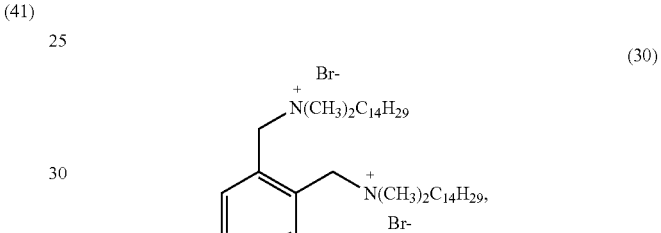

In such embodiments, it is preferred that $R_1$, $R_2$, $R_5$ and $R_6$ are each $C_{1-3}$alkyl; and $R_3$ and $R_7$ are each independently $C_{8-18}$alkyl.

In other such embodiments, it is preferred that $R_1$, $R_2$, $R_5$ and $R_6$ are each methyl; and $R_3$ and $R_7$ are each independently $C_{12-14}$alkyl.

In still other such embodiments, it is preferred that $R_1$ and $R_2$ are each $C_{1-3}$alkyl; $R_3$ is $C_{8-18}$alkyl; and $R_5$, $R_6$, and $R_7$, together with the nitrogen atom to which they are attached, form pyridinium.

In yet other such embodiments, it is preferred that $R_1$ and $R_2$ are each methyl; and $R_3$ is $C_{12-14}$alkyl.

Preferred compounds of such embodiments include:

(30)

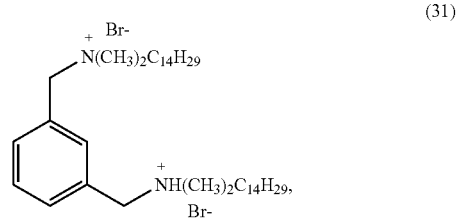

(31)

(32)

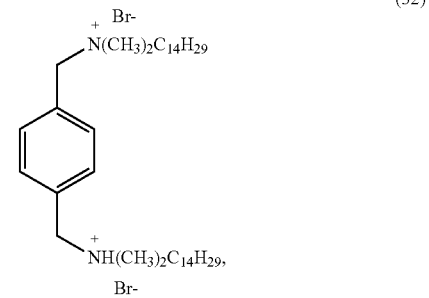

(37)

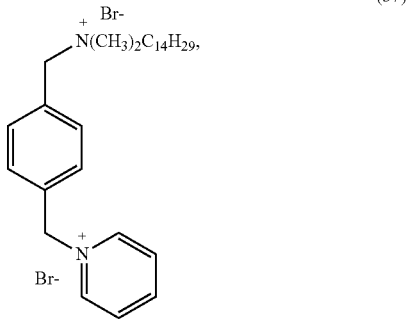

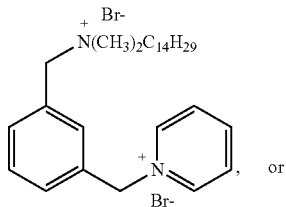
(36)

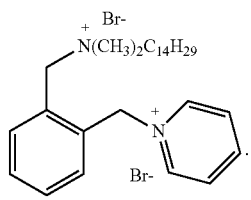
(35)

Other embodiments of the invention include pharmaceutical compositions that include compounds of formula I wherein m is 1; n is 1; p is 1; and t is 0. In such embodiments, it is preferred that $R_1$, $R_2$, $R_5$, $R_6$, $R_8$ and $R_9$ are each independently $C_{1-3}$alkyl; and $R_3$, $R_7$, and $R_{10}$ are each independently $C_{8-18}$alkyl.

In other such embodiments, it is preferred that $R_1$, $R_2$, $R_5$, $R_6$, $R_8$ and $R_9$ are each methyl; and $R_3$, $R_7$, and $R_{10}$ are each independently $C_{12-14}$alkyl.

Preferred compounds for use in pharmaceutical compositions of the invention include

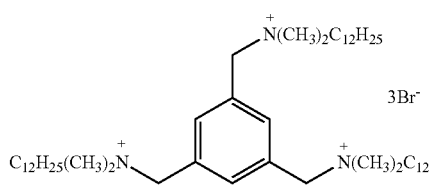
(22)

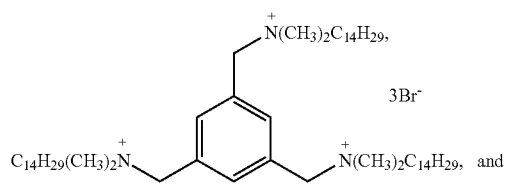
(23)

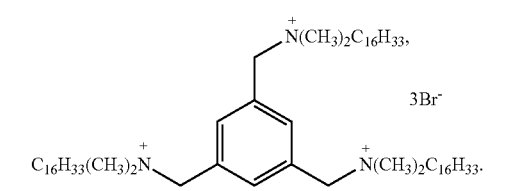
(24)

In yet other such embodiments, it is preferred that $R_1$, $R_2$, $R_5$, and $R_6$, are each independently $C_{1-3}$alkyl; $R_3$ and $R_7$ are each independently $C_{8-18}$alkyl; and $R_8$, $R_9$, and $R_{10}$, together with the nitrogen atom to which they are attached, form pyridinium.

Preferred compounds for use in pharmaceutical compositions of the invention include those in the following table:

![structure]

| Comp. No. | $R_3$ | $R_7$ |
|---|---|---|
| 25 | —$C_8H_{17}$ | —$C_8H_{17}$ |
| 26 | —$C_{10}H_{21}$ | —$C_{10}H_{21}$ |
| 27 | —$C_{12}H_{25}$ | —$C_{12}H_{25}$ |
| 28 | —$C_{14}H_{29}$ | —$C_{14}H_{29}$ |
| 29 | —$C_{16}H_{33}$ | —$C_{16}H_{33}$ |

In all of the foregoing embodiments of the invention, it is preferred that X is Br.

Also within the scope of the invention are methods of inhibiting bacterial growth comprising contacting a bacteria with any of the compounds of the invention described herein. Preferred bacteria include *Staphylococcus aureus, Entercoccus faecalis, Escherichia coli, Pseudomonas aeruginosa* or a combination thereof.

As used herein, "alkyl" refers to a straight or branched chain hydrocarbon having from one to 22 carbon atoms. Examples of alkyl groups include methyl, ethyl, propyl, isopropyl, butyl, isobutyl, tert-butyl, pentyl, isopentyl, hexyl, and the like.

As used herein, "pyridinium" refers to the cationic form of pyridine.

As used herein, "substituted pyridinium" refers to the cationic form of pyridine wherein one or more carbon atoms of the pyridine ring is substituted with, for example, $C_{1-6}$alkyl, $C_{6-10}$aryl, such as phenyl or naphthyl, or a heteroaryl such as pyridyl.

As used herein, "halogen" refers to F, Cl, Br, and I.

As used herein, "tartrate" refers to the negatively charged form of tartaric acid.

The applicable carrier or diluent may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety. Suitable examples of liquid carriers and diluents include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof. The compounds of the invention may be administered in an effective amount by any of the conventional techniques well-established in the medical field. The compounds employed in the methods of the present invention including, for example, the compounds of formula I may be administered by any means that results in the contact of the active agents with the agents' site or sites of action in the body of a patient. The compounds may be administered by any conventional means available.

Compounds of the invention can be prepared according to methods known in the art, for example, as described in K. Z. Roszak et al. *Biscationic bicephalic (double-headed) amphiphiles with an aromatic spacer and a single hydrophobic tail,* J. Colloid and Interface Science 331 (2009) 560-564, the entirety of which is incorporated herein. Exemplary methods for preparing certain embodiments are the invention are described herein. Those skilled in the art can readily modify the procedures described herein to prepared compounds within the full scope of the invention.

Accordingly, a series of commercially available dimethylphenols as well as p-cresol were exposed to Williamson ether synthesis conditions, resulting in phenol alkylation in high yields (compound A, 72-99%, Scheme 1 and accompanying table). Light-promoted benzylic bromination (NBS, benzoyl peroxide) subsequently generated the corresponding benzylic bromides B in low yields. Exposure to trimethylamine in ethanol at reflux completed the syntheses of these amphiphiles (C), which were purified by recrystallization (EtOH/H$_2$O) in good yield.

| Compound | m | Substitution | Chain length (R) | % yield of A | % yield of bromide B | % yield of compound |
|---|---|---|---|---|---|---|
| 1 | 2 | 2,3 | C$_{14}$H$_{29}$ | 78% | 39% | 68% |
| 2 | 2 | 2,4 | C$_{14}$H$_{29}$ | 84% | 31% | 11% |
| 3 | 2 | 2,5 | C$_{10}$H$_{21}$ | 90% | 14% | 76% |
| 4 | 2 | 2,5 | C$_{12}$H$_{25}$ | 88% | 25% | 81% |
| 5 | 2 | 2,5 | C$_{14}$H$_{29}$ | 86% | 23% | 87% |
| 6 | 2 | 2,5 | C$_{16}$H$_{33}$ | 72% | 28% | 78% |
| 7 | 2 | 2,5 | C$_{18}$H$_{37}$ | 78%* | 25% | 83% |
| 8 | 2 | 2,6 | C$_{14}$H$_{29}$ | 99% | 8% | 40% |
| 11 | 1 | para (4) | C$_{10}$H$_{21}$ | 92% | 30% | 76% |
| 12 | 1 | para (4) | C$_{14}$H$_{29}$ | 80% | 15% | 74% |

*= acetone used as solvent.

Scheme 1

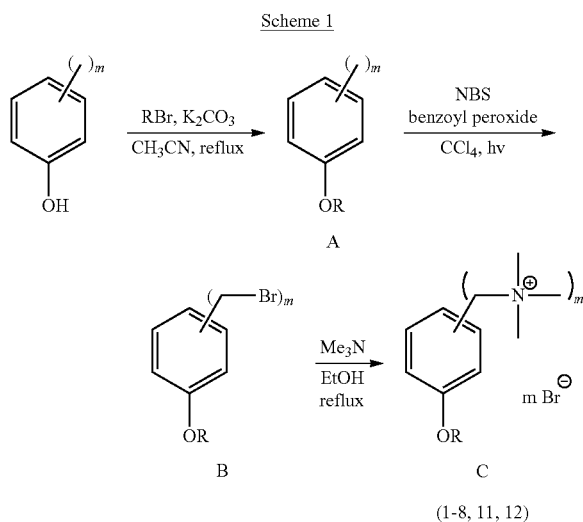

Compounds 9 and 10 can be prepared via an alternate method, as benzylic bromination of the 3,5-dimethylalkoxyphenol derivatives yielded a complex mixture of products. Compounds 9 and 10 were prepared from 5-hydroxyisophthalate dimethylester (14, Scheme 2). Accordingly, Williamson ether synthesis (tetradecyl or hexadecyl bromide, K$_2$CO$_3$, CH$_3$CN, reflux) followed by lithium aluminum hydride reduction yielded the diol (D). Subsequent reaction with phosphorus tribromide provided bis-benzylic bromides B, which were transformed to the corresponding trimethylammonium cations in good yield as described above.

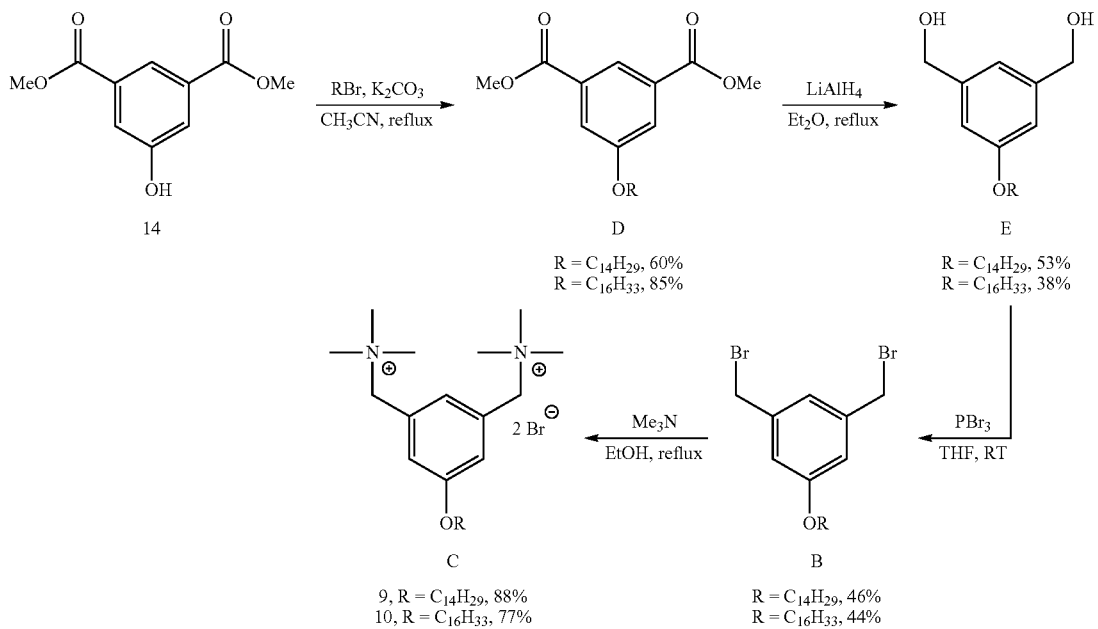

Scheme 2

Other compounds of the invention, for example, compounds 21 to 29 can be prepared according to the sequence set forth in Scheme 3.
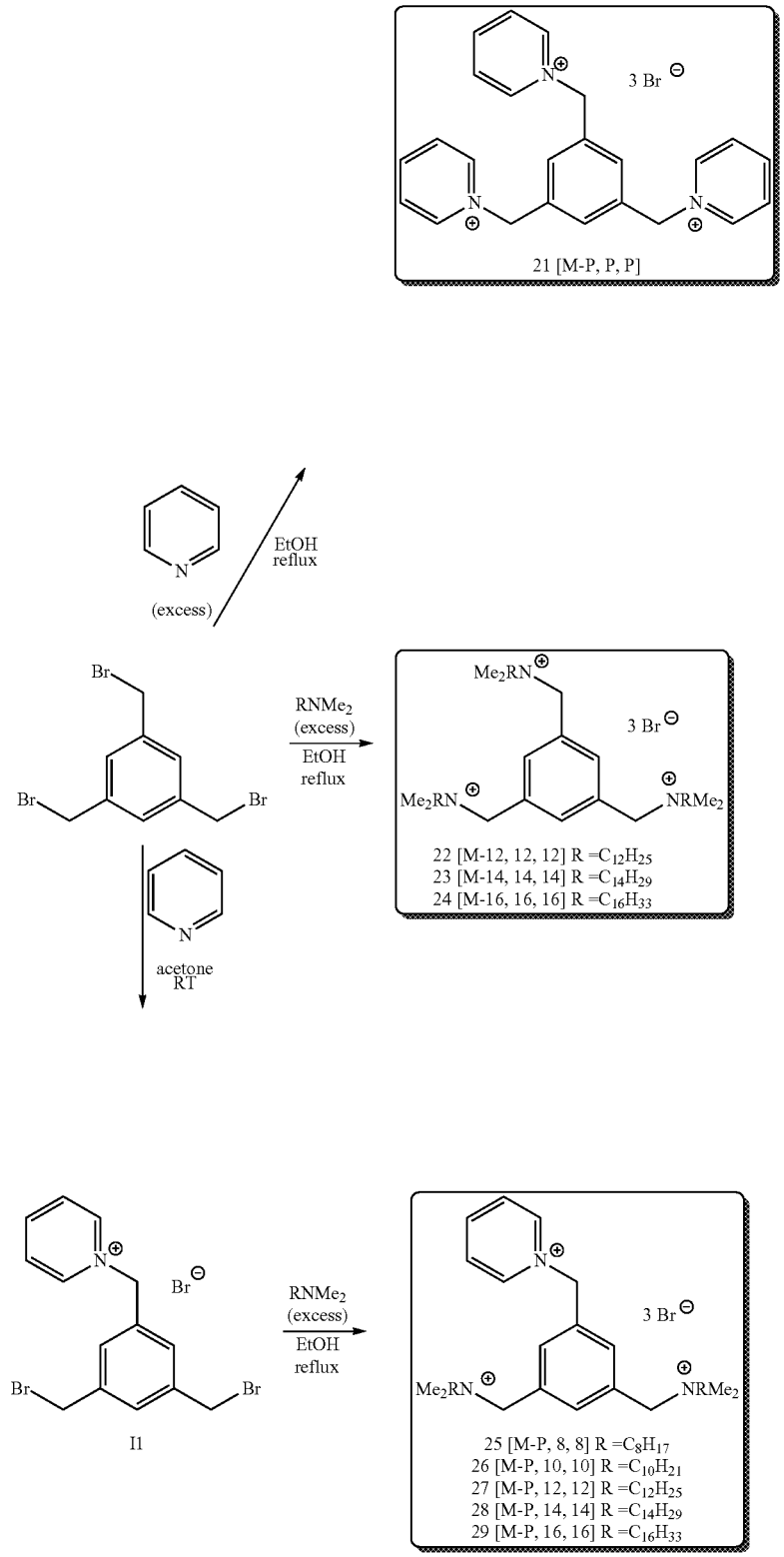

Other compounds of the invention, for example, compounds 30, 31, 32, 35, 36, and 37 can be prepared according to the sequence set forth in Scheme 4.

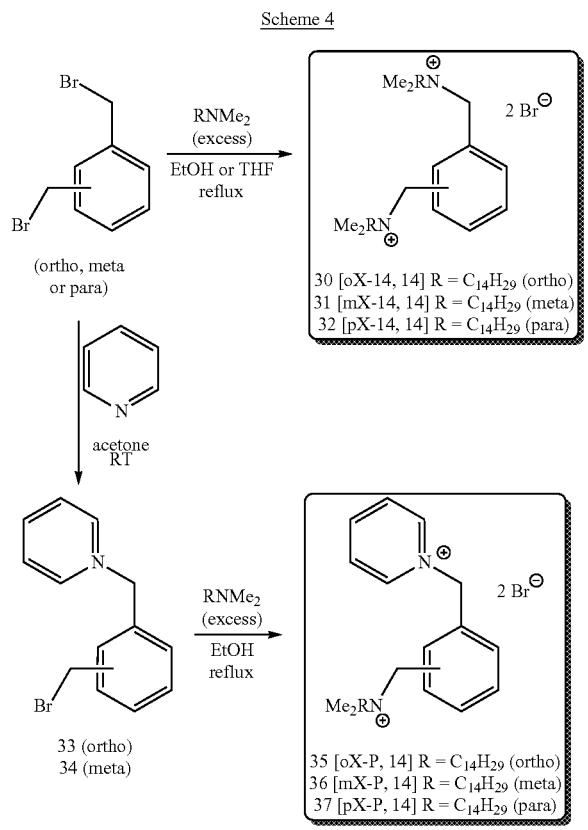

Scheme 4

Other compounds of the invention, for example, compound 41, can be prepared according to the sequence set forth in Scheme 5.

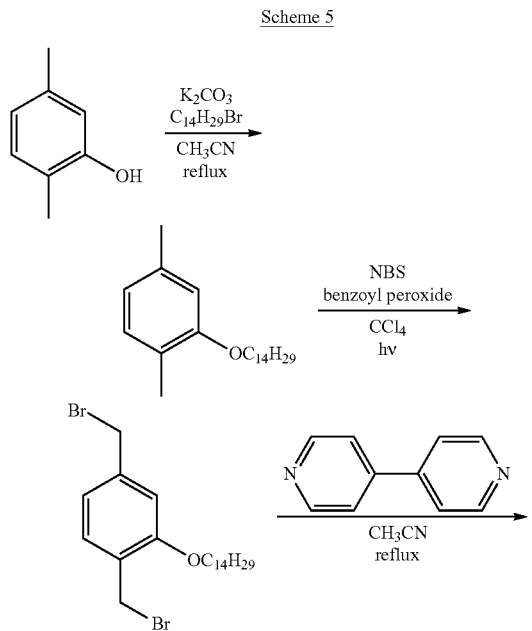

Scheme 5

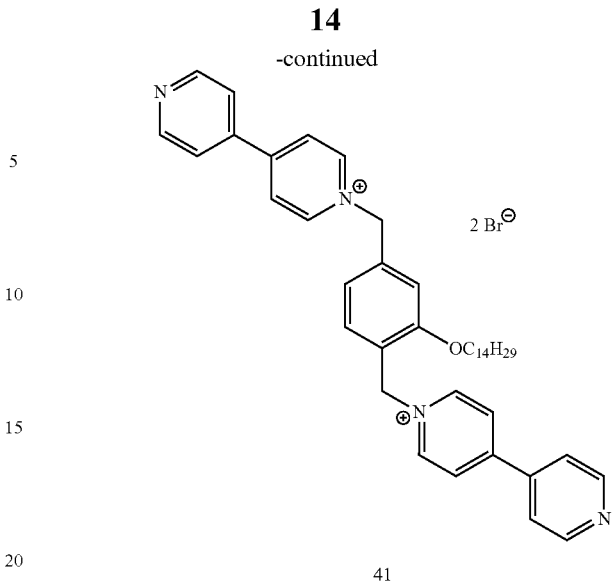

41

The compounds of the invention are useful for inhibiting the growth of bacteria by contacting a bacteria with a compound of formula I. Preferably, the compound of formula I is formulated into a pharmaceutical composition for use in inhibiting bacterial growth. The invention is particularly useful in inhibiting the growth of, for example, *Staphylococcus aureus, Entercoccus faecalis, Escherichia coli, Pseudomonas aeruginosa* or a combination thereof.

The growth of other bacteria can also be inhibited using the compounds and compositions of the invention, for example, *Salmonella* species, *Shigella* species, *Streptococcus pyogenes*, and *Haemophilus influenzae*.

All compounds except for 2,5-C10 (3) and SDS were effective at killing *S. aureus* at low micromolar concentrations, with compounds 2,3-C14 (1), 2,4-C14 (2), 3,5-C14 (9), MC10 (11), and MC14 (12) effective at <10 µM. against *E. faecalis*, compounds 1, 2, and 5-12 had MIC and MBC values at 16-50 µM, with 4 effective at 125 µM. The concentration of compounds necessary to kill *E. coli* were between those necessary to kill *E. faecalis* and *P. aeruginosa*, generally between 31-63 µM.

Compounds 2,4-C14 (2) and 3,5-C14 (9) had the lowest MIC and MBC values against all 4 strains, with 3,5-C16 (10) and MC10 (11) being nearly as effective across the strains. The monocationic compounds MC10 (11) and MC14 (12) were much more effective at inhibiting Gram-positive organisms than Gram-negatives.

In addition to determining MIC and MBC values, compounds were assayed for the time necessary to kill $2.5 \times 10^6$ cfu/mL. The time kill results were similar for *S. aureus* and *E. faecalis*. 2,5-C18 (7), 3,5-C16 (10), and MC14 (12) each killed within 15 min, while MC10 (11) killed within 30 min. *E. coli* was killed by 3,5-C16 (10) within 15 min, while 2,3-C14 (1), 2,5-C18 (7), and MC10 (11) killed within 30 min Although a number of compounds were effective at killing within 72 h, clearly 3,5-C16 (10) was the most efficient at killing the 3 strains tested, while 2,5-C18 (7) was nearly as efficient. MC14 (12) was very effective against the Gram-positive strains, but ineffective against *E. coli*.

Additionally, aliquots of cells killed by the compounds were placed on slides and visualized microscopically to determine if any intact cells were present after treatment. Visual inspection suggested that the effective compounds kill via cell lysis. MICs and MBCs of preferred compounds of the invention are set forth in Table 3. Time killing of bacterial strains by preferred compounds of the invention are set forth in Table 4.

TABLE 3

MICs and MBCs (μM) of Compounds of the Invention

| Compound | S. aureus (G+) | E. faecalis (G+) | E. coli (G−) | P. aeruginosa (G−) |
|---|---|---|---|---|
| 2,3-C14 (1) | 6 | 31 | 63 | 125 |
| 2,4-C14 (2) | 6 | 16 | 31 | 125 |
| 2,5-C10 (3) | 250 | 500 | >500 | >500 |
| 2,5-C12 (4) | 31 | 125 | 500 | >500 |
| 2,5-C14 (5) | 16 | 31 | 63 | 250 |
| 2,5-C16 (6) | 16 | 50 | 63 | 125 |
| 2,5-C18 (7) | 16 | 31 | 63 | 250 |
| 2,6-C14 (8) | 16 | 50 | 125 | 500 |
| 3,5-C14 (9) | 8 | 31 | 31 | >63 |
| 3,5-C16 (10) | 16 | 31 | 63 | >63 |
| MC10 (11) | 8 | 16 | 63 | 250 |
| MC14 (12) | 6 | 16 | >500 | >500 |
| SDS (13) | 250 | 500 | >500 | >500 |
| 2,3-C14pyr (15) | 4 | 8 | 16 | 63 |
| 3,5-C14pyr (40) | 4 | 16 | 16 | 63 |
| 2,5-C14dipyr (41) | 16 | 31 | 16 | 125 |
| 3,5-C16pyr (16) | 16 | 31 | 31 | 125 |
| mX-14,14 (31) | 4 | 6 | 47 | 125 |
| pX-14,14 (32) | 16 | 16 | 63 | 125 |
| M-P,12,12 (27) | 2 | 2 | 4 | 8 |
| M-P,14,14 (28) | 8 | 8 | 16 | 125 |
| M-P,16,16 (29) | 31 | 31 | 63 | 125 |
| M-14,14,14 (23) | 31 | 31 | 63 | 125 |

G+ = Gram-positive,
G− = Gram-negative

TABLE 4

Time Killing of Bacterial Strains by Compounds of the Invention.
Data are reported as time (h) when all cells were killed by
100 μM of compound.

| Compound | S. aureus (G+) | E. faecalis (G+) | E. coli (G−) |
|---|---|---|---|
| 2,3-C14 (1) | 1 | 24 | 0.5 |
| 2,4-C14 (2) | 1 | 2 | 1 |
| 2,5-C10 (3) | NK | NK | NK |
| 2,5-C12 (4) | NK | NK | NK |
| 2,5-C14 (5) | 48 | 48 | 72 |
| 2,5-C16 (6) | 24 | NK | 2 |
| 2,5-C18 (7) | 0.25 | 0.25 | 0.5 |
| 2,6-C14 (8) | 48 | NK | NK |
| 3,5-C14 (9) | 1 | 1 | 1 |
| 3,5-C16 (10) | 0.25 | 0.25 | 0.25 |
| MC10 (11) | 0.5 | 0.5 | 0.5 |
| MC14 (12) | 0.25 | 0.25 | NK |

NK = 100% of cells not killed after treatment. Pseudomonas aeruginosa was not tested because the MIC values for all compounds were greater than 100 μM. SDS was not used because it was not effective at 100 μM.

Also within the scope of the invention are pharmaceutical compositions comprising a compound of formula IA:

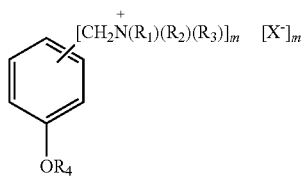

IA wherein $R_1$, $R_2$, and $R_3$ are each independently $C_{1-6}$alkyl or $R_1$, $R_2$, and $R_3$, together with the nitrogen atom to which they are attached, form a pyridinium;

m is 1 or 2;

$R_4$ is $C_{8-22}$alkyl; and

X is halogen or tartrate;

and a pharmaceutically acceptable carrier or diluent.

Preferred embodiments include pharmaceutical compositions wherein m is 1. Also within the scope of the invention are pharmaceutical compositions, wherein the compound of formula IA has the following structure:

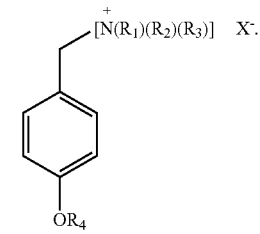

Other preferred embodiments include pharmaceutical compositions wherein m is 2.

Preferred pharmaceutical compositions comprise one or more of the following compounds:

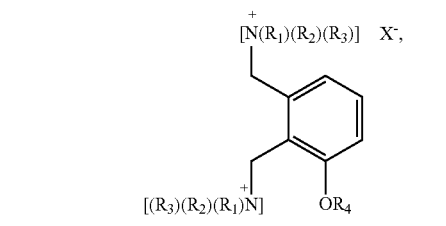

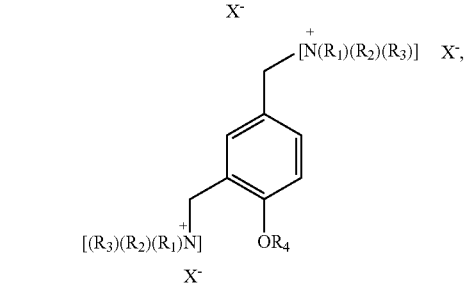

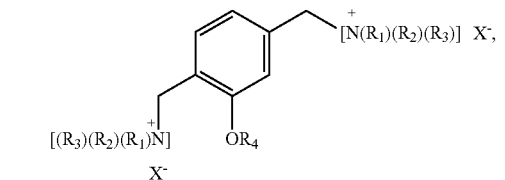

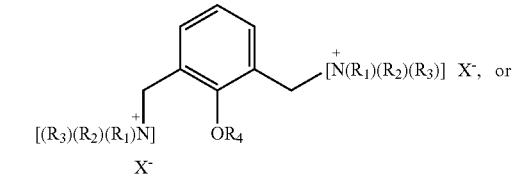

-continued

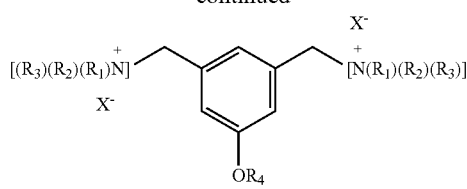

wherein $R_1$, $R_2$, and $R_3$ are each independently $C_{1-6}$alkyl or $R_1$, $R_2$, and $R_3$, together with the nitrogen atom to which they are attached, form a pyridinium;

m is 1 or 2;

$R_4$ is $C_{8-22}$alkyl; and

X is halogen or tartrate;

and a pharmaceutically acceptable carrier or diluent.

Preferred embodiments of the invention include compounds of formula IA, wherein each of $R_1$, $R_2$, and $R_3$ is $C_{1-3}$alkyl. In other embodiments, each of $R_1$, $R_2$, and $R_3$ is methyl. In yet other embodiments, $R_1$, $R_2$, and $R_3$, together with the nitrogen atom to which they are attached, form a pyridinium.

Other preferred embodiments of the invention include compounds of formula IA, wherein $R_4$ is $C_{10-18}$alkyl. Yet other embodiments include compounds wherein $R_4$ is —$C_{10}H_{21}$. In still other embodiments, $R_4$ is —$C_{12}H_{25}$. In still other embodiments are compounds of formula IA, wherein $R_4$ is —$C_{14}H_{29}$. Also preferred are compounds of formula IA, wherein $R_4$ is —$C_{16}H_{33}$. Preferred pharmaceutical compositions also include compounds of formula IA, wherein $R_4$ is —$C_{18}H_{37}$.

Also within the scope of the invention are pharmaceutical compositions, wherein X is Br.

Preferred pharmaceutical compositions of the invention include compounds of formula IA is selected from the following Table:

| m | Substitution | $R_4$ |
|---|---|---|
| 2 | 2, 3 | —$C_{14}H_{29}$ |
| 2 | 2, 4 | —$C_{14}H_{29}$ |
| 2 | 2, 5 | —$C_{10}H_{21}$ |
| 2 | 2, 5 | —$C_{12}H_{25}$ |
| 2 | 2, 5 | —$C_{14}H_{29}$ |
| 2 | 2, 5 | —$C_{16}H_{33}$ |
| 2 | 2, 5 | —$C_{18}H_{37}$ |
| 2 | 2, 6 | —$C_{14}H_{29}$ |
| 2 | 3, 5 | —$C_{14}H_{29}$ |
| 2 | 3, 5 | —$C_{16}H_{33}$ |
| 1 | 4 | —$C_{10}H_{21}$ |
| 1 | 4 | —$C_{14}H_{29}$ |

Other preferred pharmaceutical compositions of the invention include those, wherein the compound of formula IA is selected from the following Table:

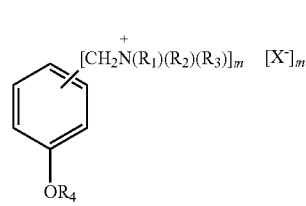

| m | Substitution | $R_4$ |
|---|---|---|
| 2 | 2, 3 | —$C_{14}H_{29}$ |
| 2 | 3, 5 | —$C_{16}H_{33}$ |

Within the scope of the invention are methods of inhibiting bacterial growth comprising contacting a bacteria with a compound of formula IA. In preferred embodiments, the bacteria is *Staphylococcus aureus, Entercoccus faecalis, Escherichia coli, Pseudomonas aeruginosa* or a combination thereof.

Also within the scope of the invention are compounds of formula IB:

IB $$[CH_2N(R_1)(R_2)(R_3)]_m \quad [X^-]_m$$

(on phenyl ring with $OR_4$)

wherein $R_1$, $R_2$, and $R_3$ are each independently $C_{1-6}$alkyl or $R_1$, $R_2$, and $R_3$, together with the nitrogen atom to which they are attached, form a pyridinium;

m is 1 or 2; wherein when m is 1, the —$CH_2$—[$N(R_1)(R_2)(R_3)$] group is at the 2, 3, 5, or 6 position of the phenyl ring and when m is 2, the —$CH_2$—[($N(R_1)(R_2)(R_3)$)] groups are not at the 2,5 positions of the phenyl ring;

$R_4$ is $C_{8-22}$alkyl; and

X is halogen or tartrate.

The following experimental details are exemplary only and are not intended to limit the scope of the invention.

Experimental Section

Bacterial Strains and Culture Conditions.

Bacterial strains *Staphylococcus aureus* subsp. *aureus* ATCC® 29213™, *Entercoccus faecalis* ATCC® 29212™, *Escherichia coli* ATCC® 25922™, and *Pseudomonas aeruginosa* strain Boston 41501 ATCC® 27853™ were obtained from the American type Culture Collection (ATCC, Manassas, Va., USA). *S. aureus* and *E. faecalis* are Gram-positive pathogens, *P. aeruginosa* is a Gram-negative pathogen, and *E. coli* is a non-pathogenic Gram-negative organism. All strains are reference strains for the Clinical and Laboratory Standards Institute (CLSI) for antimicrobial susceptibility testing of nonfastidious bacteria, and were grown in Mueller-Hinton broth at 37° C. as recommended (Wayne, Pa. National Committee for Clinical Laboratory Standards (2009) Methods for Dilution Antimicrobial Tests for Bacteria That Grow Aerobically—Approved Standard M07-A8).

Broth Microdilution MIC and MBC Determination.

The broth microdilution for determining the MIC and MBC of antimicrobial compounds was performed as previously described in Wayne, supra. Briefly, all compounds were serially diluted and 100 µl of each dilution was added to microtiter plate wells in triplicate. Overnight cultures of bacterial cells were diluted to a final inoculum of approximately $5 \times 10^6$ cfu/mL, and 100 µl of this suspension was added to all wells yielded $5 \times 10^5$ cfu/well. Cell concentrations and viability were verified by serial dilution and plating for each experiment. Microtiter plates were incubated at 37° C. for 72 h. The MIC was determined as the lowest concentration of compound to completely inhibit growth as detected by the unaided eye. From each set of triplicate wells, 100 µl was then plated on Todd-Hewitt agar (THA, Becton, Dickinson and Company, Sparks, Md., USA) and incubated for 24 h and examined to determine the MBC values for each compound. The MBC was determined as the lowest concentration of compound at which there were no colonies growing on the plate. MIC and MBC experiments were performed a minimum of 3 times for each organism.

Bacterial Killing Assays.

To determine the relative temporal effectiveness of the synthesized amphiphiles, overnight cultures were diluted in broth to a concentration of $2.5 \times 10^6$ cfu/ml. Compounds were added to the cultures to a final concentration of 100 µM, and tubes were incubated at room temperature. At 15, 30, 60, 90, 120, 180 min, 24, 48, and 72 h, one-hundred microliter aliquots were plated on THA plates, and the plates were incubated overnight at 37° C. Data reported are times when no colonies were observed growing on plates after overnight incubation. Additionally, 100 µl of cells treated with compounds for 72 h were placed on slides, Gram-stained, and visualized microscopically to determine if intact cells were still present after treatment.

MIC values for the compounds of the invention were determined by the broth microdilution method as described herein. MICs were determined as the lowest concentration which prevented visible growth at 72 h. After microtiter plates were incubated and MICs determined, aliquots from each of the wells were placed on TSA plates and incubated to determine the MBC values for each of the compounds. The MBC was determined as the lowest concentration of compound at which there were no colonies growing on the plate. The MBC and MIC values were identical in every case, indicating that the compounds are effective at killing the bacteria, not just inhibiting growth. SDS was used for comparison in these studies. For the MICs and MBCs, there was variability both with various compounds against individual strains, and with a single compound across strains.

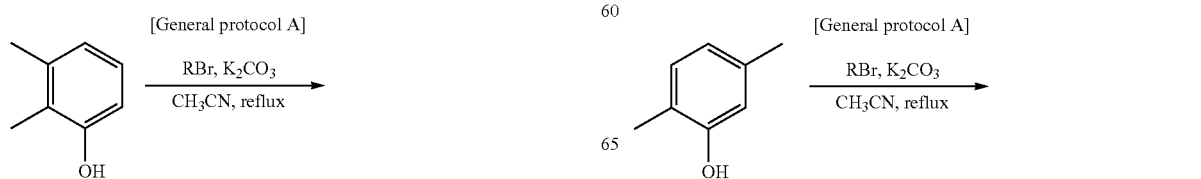

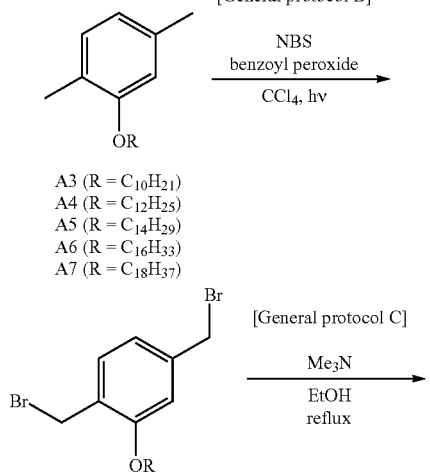
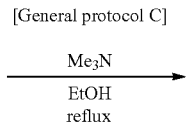
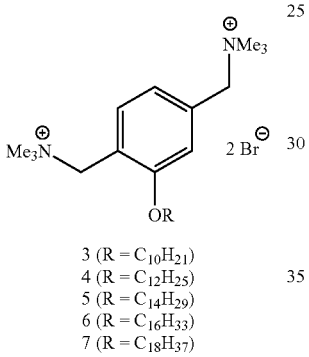
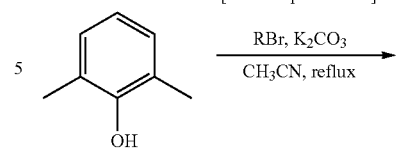
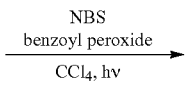
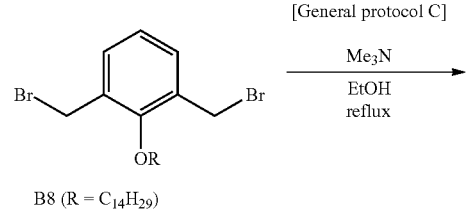
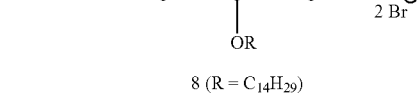
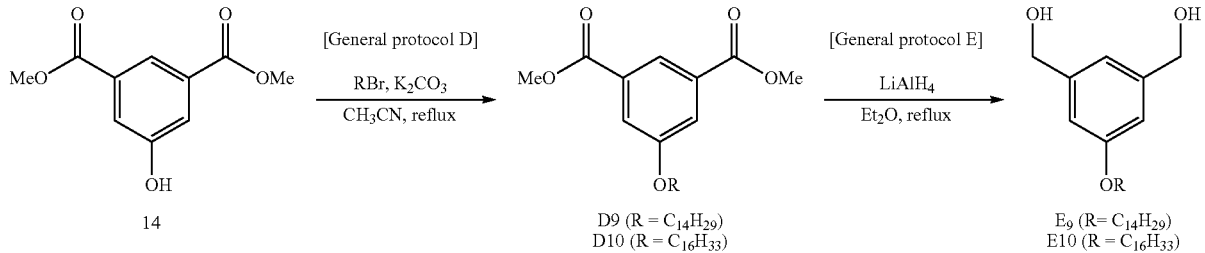
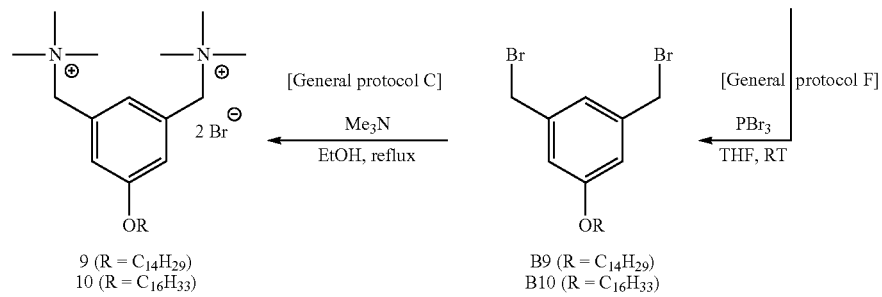

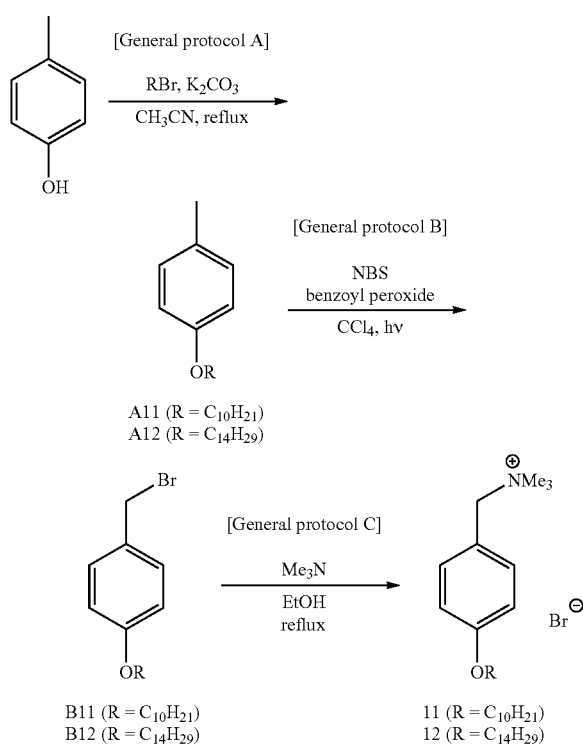

Synthesis and Analysis.

All solvents and reagents were used as received from the indicated chemical supplier unless otherwise specified. Melting points for solids were measured using a Mel-Temp apparatus with a digital thermometer (uncorr). Nuclear magnetic resonance spectra were recorded using one of the following instruments, as noted: 600 ($^1$H: 600 MHz, $^{13}$C: 150 MHz) or 400 ($^1$H: 400 MHz, $^{13}$C: 100 MHz). The solvent residual peak was used as a reference. Coupling constants are estimated to be correct within ±0.1 Hz. High-resolution mass spectra (HRMS) were recorded on a AccuTOF time-of-flight mass spectrometer using either a Direct Analysis in Real Time (DART) interface or electrospray ionization (ESI) interface, as noted, in positive ion mode.

Synthesis of 1-8, 11, 12.

Compounds 1-8, 11, and 12 were prepared via a three step synthesis starting from the corresponding methyl phenol derivative as shown in Scheme S1 using General protocols A-C, described below. Specific synthetic details for each derivative not previously reported are presented subsequently.

Synthesis of 9, 10.

Compounds 9 and 10 were prepared via a four step synthesis starting from dimethyl-5-hydroxyisophthalate (14) as shown in Scheme S1 using General protocols D, E, F and C, described below. Specific synthetic details for each derivative are presented subsequently.

General Protocol A: Williamson Ether Synthesis Starting from X,Y-Dimethyl Phenol or p-Cresol [Y.-Z. Lee, X., Chen, S.-A. Chen, P.-K. Wei, W.-S. Fann, *J. Am. Chem. Soc.* 2001, 123, 2296].

The alkyl bromide, phenol derivative and potassium carbonate were combined in a round bottom flask in acetonitrile or acetone, as noted. The flask was equipped with a stir-bar, and a water-cooled condenser and protected under a nitrogen atmosphere. The mixture was heated at reflux for one to three days. Synthetic progress was monitored by the disappearance of the signal (triplet) from the C1 hydrogens on the alkyl bromide (~3.5 ppm) in $^1$H NMR. Upon completion, the reaction was removed from heat and excess K$_2$CO$_3$ was removed by gravity filtration (rinsed with CH$_2$Cl$_2$). The crude product was concentrated in vacuo and the resulting material was dissolved in CH$_2$Cl$_2$, washed with 1 M NaOH (2×, to remove unreacted phenol derivative), dH$_2$O (2×) and brine (1×), dried over Na$_2$SO$_4$, gravity filtered, and concentrated in vacuo to remove the solvent. If needed, the product was purified by column chromatography (as noted). The material was of sufficient purity (by $^1$H and $^{13}$C NMR) to be used in the subsequent reactions.

General Protocol B: Benzylic Bromination [Y.-Z. Lee, X., Chen, S.-A. Chen, P.-K. Wei, W.-S. Fann, *J. Am. Chem. Soc.* 2001, 123, 2296].

All glassware was dried in an oven overnight and flushed with N$_2$ (g) prior to use. A solution of the synthesized aryl alkyl ether (A1-A8, A11 or A12, as noted) in carbon tetrachloride was prepared in a round bottom flask equipped with a water-cooled condenser, magnetic stir bar and protected with under a nitrogen atmosphere. N-bromosuccinimide (NBS) and benzoyl peroxide (cat) were added and the reaction was either heated to reflux on an oil bath or reacted at room temperature under irradiation from a 300 W/82V tungsten halogen lamp (as noted). Reaction progress was monitored by the disappearance of the insoluble NBS at the bottom of the flask and the appearance of the lower density insoluble succinimide byproduct that floated to the surface of the reaction mixture. After filtration of the succinimide, the solvent was removed in vacuo. The crude product was recrystallized from n-hexane.

General Protocol C: Menchutkin Reaction.

The bis-benzylbromide derivate (B1-B10, as noted) or benzyl bromide derivative (B11 or B12, as noted) was suspended in absolute ethanol in a two-neck round-bottom flask which was attached to a nitrogen (g) protected water-cooled condenser. Trimethylamine (33 wt. % in ethanol) was added via syringe, the second neck was sealed with a glass stopper and the reaction was heated to reflux on an oil bath. The solid starting material dissolved upon heating. After at least four hours under reflux, excess NMe$_3$ and EtOH were allowed to evaporate under a flow of N$_2$ gas by removing the stopper from the second neck. The residual material was taken up in absolute EtOH, transferred to a clean round bottom flask and the solvent was removed in vacuo. The product was recrystallized from EtOH/Et$_2$O. Residual volatile material was removed by vacuum drying over P$_2$O$_5$ at 80-115° C.

General Protocol D: Williamson Ether Synthesis Starting from dimethyl-5-hydroxyisophthalate.

The alkyl bromide, dimethyl-5-hydroxyisophthalate (14) and potassium carbonate were combined in a round bottom flask in acetonitrile. The flask was equipped with a stir-bar, and a water-cooled condenser and protected under a nitrogen atmosphere. The mixture was heated at reflux for one to three days. Synthetic progress was monitored by the disappearance of the signal (triplet) from the C1 hydrogens on the alkyl bromide (~3.5 ppm) in $^1$H NMR. Upon completion, the reaction was removed from heat and excess K$_2$CO$_3$ was removed by gravity filtration (rinsed with CH$_2$Cl$_2$). The crude product was concentrated in vacuo and the resulting material was dissolved in CH$_2$Cl$_2$, washed with 1 M NaOH (2×, to remove unreacted 14), dH$_2$O (2×) and brine (1×), dried over Na$_2$SO$_4$, gravity filtered, and concentrated in vacuo to remove the solvent. If needed, the product was purified by column chromatography (as noted). The material was of sufficient purity (by $^1$H and $^{13}$C NMR) to be used in the subsequent reactions.

General Protocol E: Ester Reduction.

All glassware was dried in an oven overnight and flushed with $N_2$ (g) prior to use. A solution of diester D9 or D10 (1 equiv.) in dry $Et_2O$ was prepared in a 100-mL round bottom flask. In a second round bottom flask equipped with a magnetic stir bar and a water-cooled condenser, lithium aluminum hydride (2.2 equiv, 95% Acros) was suspended in dry $Et_2O$. The ethereal diester solution was added dropwise to the reaction flask via syringe. The reaction was run under reflux for 3 hours and subsequently quenched with the addition of 5 mL NaOH (1M), and 20 mL $H_2O$. The $Et_2O$ was removed from the reaction flask via rotary evaporation. The product was purified by recrystallization from EtOH and trituration from benzene and hexanes.

General Protocol F: Substitution Using Phosphorus Tribromide.

Phosphorus tribromide ($PBr_3$) (2.2 equiv, 99% Acros) was added via syringe to a THF solution of bis-benzyl alcohol E10 or E11 (1 equiv) in a round bottom flask equipped with nitrogen and a magnetic stir bar. After three days at room temperature, the reaction mixture was concentrated via rotary evaportaion. The resulting brown liquid was purified by column chromatography on silica using hexanes followed by an increasing gradient to EtOAc/hexanes (98/2). The desired product was obtained after removal of the solvent in vacuo.

1-tetradecyloxy-2,3-dimethylbenzene (A1)

The product was generated via general protocol A using 1-bromotetradecane (45.0 mL, 147.9 mmol), 2,3-dimethylphenol (20.15 g, 163.3 mmol), $K_2CO_3$ (81.76 g, 591.6 mmol) and $CH_3CN$ (200 mL). Yielded 36.6 g (77.7%) of a brown liquid. $^1H$ NMR ($CDCl_3$, 400 MHz) δ: 7.03 (t, $^3J$=7.8 Hz, 1H, Ar—H), 6.76 (d, $^3J$=7.4 Hz, 1H, Ar—H), 6.70 (d, $^3J$=8.1 Hz, 1H, Ar—H), 3.93 (t, $^3J$=6.5, 2H, O—C$\underline{H}_2$), 2.27 (s, 3H, Ar—C$\underline{H}_3$), 2.16 (s, 3H, Ar—C$\underline{H}_3$), 1.79 (p, $^3J$=6.9, 2H, O—CH$_2$—C$\underline{H}_2$), 1.48 (p, $^3J$=7.1, 2H, O—CH$_2$—CH$_2$—C$\underline{H}_2$), 1.27 (m, 22H), 0.88 (t, $^3J$=6.3, 3H, CH$_2$—C$\underline{H}_3$). $^{13}C$ NMR ($CDCl_3$, 100 MHz) δ: 157.20, 137.86, 125.84, 125.33, 122.08, 108.98, 68.23, 32.07, 29.86, 29.83, 29.78, 29.61, 29.58, 29.54, 26.33, 22.88, 20.17, 14.24, 11.70.

1-tetradecyloxy-2,3-bis(bromomethyl)benzene (B1)

The product was generated via general protocol B using 1-tetradecyloxy-2,3-dimethylbenzene (A1, 25.1 g, 78.1 mmol), N-bromosuccinimide (99%, 28.2 g, 158 mmol), benzoyl peroxide (38 mg, 0.16 mmol) and $CCl_4$ (850 mL). The reaction was run in 10 equal batches at room temperature under irradiation for ~60 min per batch. After two recrystallizations of the combined crude product from n-hexane 14.87 g (39.46%) of pure product was obtained as an off-white solid, m.p.=55.7-56.5° C. $^1H$ NMR ($CDCl_3$, 300 MHz) δ: 7.24 (t, $^3J$=8.0 Hz, 1H, Ar—H), 6.94 (d, $^3J$=7.5 Hz, 1H, Ar—H) 6.84 (d, $^3J$=8.2, 1H, Ar—H), 4.78 (s, 2H, Ar—C$\underline{H}_2$), 4.62 (s, 2H, Ar—C$\underline{H}_2$), 4.02 (t, $^3J$=6.4, 2H, O—C$\underline{H}_2$), 1.84 (p, 2H, O—CH$_2$—C$\underline{H}_2$), 1.54 (p, 2H, O—CH$_2$—CH$_2$—C$\underline{H}_2$), 1.26 (m, 22H), 0.88 (t, $^3J$=6.68, 3H, CH$_2$—C$\underline{H}_3$). $^{13}C$ NMR ($CDCl_3$, 150 MHz) δ: 157.65, 138.25, 129.94, 125.53, 122.76, 112.33, 109.56, 68.64, 32.28, 30.14, 29.74, 29.64, 29.39, 26.11, 23.88, 22.70, 14.21.

[(2-tetradecyloxy-o-phenylene)dimethylene]bis[trimethylamonium bromide] (1) (2,3-C14)

The product was generated via general protocol C using 1-tetradecyloxy-2,3-bis(bromomethyl)benzene (B1, 4.84 g, 10.2 mmol), $NMe_3$ (33% wt solution in EtOH, 9.70 mL, 40.6 mmol) and EtOH (100 mL). After recrystallization (EtOH/$Et_2O$) and drying the reaction produced 4.09 g (67.7%) of a white solid. $^1H$ NMR ($CD_3OD$, 300 MHz) δ: 7.71 (t, $^3J$=8.1 Hz, 1H, Ar—H), 7.43 (d, $^3J$=8.4 Hz, 1H, Ar—H), 7.37 (d, $^3J$=8.1 Hz, 1H, Ar—H) 4.93 (s, 2H, Ar—C$\underline{H}_2$), 4.85 (s, 2H, Ar—C$\underline{H}_2$), 4.16 (t, $^3J$=6.8 Hz, 2H, O—C$\underline{H}_2$), 3.17 (s, 18H, N—C$\underline{H}_3$), 1.9 (p, $^3J$=6.9 Hz, 2H, O—CH$_2$—C$\underline{H}_2$), 1.28 (m, 23H), 0.90 (t, $^3J$=6.5, 3H, CH$_2$—C$\underline{H}_3$). $^{13}C$ NMR ($CD_3OD$, 150 MHz) δ: 159.70, 132.70, 130.70, 127.20, 117.69, 115.53, 69.52, 64.85, 59.18, 52.31, 52.08, 31.71, 29.45, 29.16, 29.05, 28.74, 25.80, 22.36, 13.13. Anal. Calcd for $C_{28}H_{54}Br_2N_2O\cdot H_2O$: C, 54.90; H, 9.21; N, 4.57. Found: C, 54.89; H, 9.31; N, 4.48.

1-tetradecyloxy-2,4-dimethylbenzene (A2)

The product was generated via general protocol A using 1-bromotetradecane (44 mL, 0.149 mol), 2,4-dimethylphenol (19.5 mL, 0.164 mol), $K_2CO_3$ (82.4 g, 0.596 mol) and $CH_3CN$ (200 mL). Yielded 43.13 g (90.8%). $^1H$ NMR ($CDCl_3$, 600 MHz) δ: 7.00 (s, 1H, Ar—H), 6.94 (d, $^3J$=8.41 Hz, 1H, Ar—H), 6.75 (d, $^3J$=8.15 Hz, 1H, Ar—H), 3.97 (t, $^3J$=6.46 Hz, 2H, OC$\underline{H}_2$), 2.31 (s, 3H, Ar—C$\underline{H}_3$), 2.26 (s, 3H, Ar—C$\underline{H}_3$), 1.83 (p, $^3J$=7.3 Hz, 2H, O—CH$_2$—C$\underline{H}_2$), 1.52 (p, $^3J$=7.6 Hz, 2H, O—CH$_2$—CH$_2$—C$\underline{H}_2$), 1.44-1.28 (m, 22H), 0.95 (t, $^3J$=7.05, 3H, CH$_2$—C$\underline{H}_3$). $^{13}C$ NMR (150 MHz) δ: 155.24, 131.45, 129.20, 126.88, 126.66, 111.08, 68.17, 53.41, 32.02, 31.90, 29.97, 29.79, 29.78, 29.76, 29.52, 29.50, 29.46, 26.24, 22.78, 20.47, 16.19, 14.19.

1-tetradecyloxy-2,4-bis(bromomethyl)benzene (B2)

The product was generated via general protocol B using 1-tetradecyloxy-2,4-dimethylbenzene (A2, 20.2 g, 63.4 mmol), N-bromosuccinimide (99%, 22.8 g, 127 mmol), benzoyl peroxide (0.314 g, 1.30 mmol) and $CCl_4$ (680 mL). The reaction was run in 8 equal batches at room temperature under irradiation for 30-60 min per batch. After two recrystallizations of the combined crude product from n-hexane 6.66 g (22.3%) of pure product was obtained as a blue solid, m.p.=62.9° C. $^1H$ NMR ($CDCl_3$, 400 MHz) δ: 7.36 (d, $^3J$=2.3 Hz, 1H, Ar—H), 7.30 (dd, $^3J$=2.3, $^4J$=8.5, 1H, Ar—H), 6.82 (d, $^3J$=8.5, 1H, Ar—H), 4.53 (s, 2H, Ar—C$\underline{H}_2$—Br), 4.47 (s, 2H, Ar—C$\underline{H}_2$—Br), 4.03 (t, $^3J$=6.3 Hz, 2H, OC$\underline{H}_2$), 1.83 (p, $^3J$=7.0 Hz, 2H, OCH$_2$C$\underline{H}_2$), 1.49 (p, $^3J$=7.5 Hz, 2H, OCH$_2$CH$_2$C$\underline{H}_2$), 1.36-1.26 (m, 22H), 0.88 (t, $^3J$=7.0 Hz, 3H, CH$_2$C$\underline{H}_3$).

[(6-tetradecyloxy-m-phenylene)dimethylene]bis[trimethylamonium bromide] (2) (2,4-C14)

The product was generated via general protocol C using 1-tetradecyloxy-2,4-bis(bromomethyl)benzene (B2, 4.00 g, 8.40 mmol), $NMe_3$ (33% wt solution in EtOH, 12.0 mL, 50.4 mmol) and EtOH (200 mL). After recrystallization (EtOH/$Et_2O$) and drying the reaction produced 4.99 g of a white solid. Anal. Calcd for $C_{28}H_{54}Br_2N_2O\cdot 2H_2O$: C, 53.33; H, 9.27; N, 4.44. Found: C, 53.35; H, 9.16; N, 4.34.

A3-A7, B3-B7, 3-7 (2,5-C10-2,5-C18).

Synthetic details and analyses of these compounds have previously been published. [Roszak, K. Z.; Torcivia, S. L.; Hamill, K. M.; Hill, A. R.; Radloff, K. R.; Crizer, D. M.; Middleton, A. M.; Caran, K. L. *J. Colloid Interface Sci.,* 2009, 331, 560-5641.]

1-tetradecyloxy-2,6-dimethylbenzene (A8)

The product was generated via general protocol A using 1-bromotetradecane (44.7 mL, 0.147 mol), 2,6-dimethylphenol (20.0 g, 0.162 mol), K$_2$CO$_3$ (81.3 g, 0.588 mol) and CH$_3$CN (150 mL). Yielded 46.5 g (99.3%) of a yellow/orange liquid. $^1$H NMR (CDCl$_3$, 400 MHz) δ: 7.01 (d, $^4$J=7.3 Hz, 2H, Ar—H), 6.91 (t, $^3$J=6.8 Hz, 3H, Ar—H), 3.76 (t, $^3$J=6.7 Hz, 2H, OCH$_2$), 2.28 (s, 6H, Ar—CH$_3$), 1.81 (p, $^3$J=7.1 Hz, 2H, OCH$_2$CH$_2$), 1.50 (p, $^3$J=7.4 Hz, 2H, OCH$_2$CH$_2$CH$_2$), 1.36-1.27 (m, 22H), 0.89 (t, $^3$J=6.9 Hz, 3H, CH$_2$CH$_3$). $^{13}$C NMR (CDCl$_3$, 100 MHz) δ: 156.08, 130.95, 128.71, 123.54, 77.32, 77.00, 76.68, 72.28, 31.93, 30.44, 29.70, 29.68, 29.66, 29.63, 29.57, 29.37, 26.16, 22.69, 16.26, 14.12.

1-tetradecyloxy-2,6-bis(bromomethyl)benzene (B8)

The product was generated via general protocol B using 1-tetradecyloxy-2,6-dimethylbenzene (A8, 32.5 g, 102 mmol), N-bromosuccinimide (99%, 36.3 g, 204 mmol), benzoyl peroxide (0.494 g, 2.04 mmol) and CCl$_4$ (1105 mL). The reaction was run in 13 equal batches under irradiation for 30-60 min per batch. After four recrystallizations of the combined crude product from n-hexane, 8.314 g (18.5%), of the pure product was obtained as a white solid, mp=59.3-59.8° C. $^1$H NMR (CDCl$_3$, 400 MHz) δ: 7.37 (d, $^3$J=7.62 Hz, 2H, Ar—H), 7.11 (t, $^3$J=7.65, 1H, Ar—H), 4.55 (s, 4H, Ar—CH$_2$—Br), 4.10 (t, $^3$J=6.62 Hz, 2H, OCH$_2$), 1.90 (p, $^3$J=7.54 Hz, 2H, OCH$_2$CH$_2$), 1.55 (p, $^3$J=7.35 Hz, 2H, OCH$_2$CH$_2$CH$_2$), 1.43-1.22 (m, 24H), 0.88 (t, $^3$J=6.97 Hz, 3H, CH$_2$CH$_3$). $^{13}$C NMR (150 MHz) δ: 155.73, 132.26, 132.10, 132.03, 129.06, 124.92, 124.19, 73.37, 31.96, 30.35, 29.74, 29.72, 29.70, 29.65, 29.63, 29.53, 29.41, 28.68, 27.76, 26.06, 25.96, 22.73, 16.36, 14.18.

[(2-tetradecyloxy-m-phenylene)dimethylene]bis[trimethylamonium bromide] (8) (2,6-C14)

The product was generated via general protocol C using 1-tetradecyloxy-2,6-bis(bromomethyl)benzene (B8, 8.00 g, 16.7 mmol), NMe$_3$ (33% wt solution in EtOH, 24.0 mL, 100 mmol) and EtOH (400 mL). After recrystallization (EtOH/Et$_2$O) and drying the reaction produced 5.53 g (55.6%) of a white solid, mp=221.9-224.9° C. (dec). $^1$H NMR (MeOD, 600 MHz) δ: 7.81 (d, $^3$J=7.70 Hz, 2H, Ar—H), 7.48 (t, $^3$J=7.70 Hz, 1H, Ar—H), 4.58 (s, 4H, Ar—CH$_2$—N), 3.93 (t, $^3$J=7.13 Hz, 2H, O—CH$_2$), 3.18 (s, 18H, N—CH$_3$), 1.98 (p, $^3$J=7.62 Hz, 2H, O—CH$_2$—CH$_2$), 1.53-1.23 (m, 24H), 0.89 (t, $^3$J=7.0 Hz, 3H, CH$_2$—CH$_3$). $^{13}$C NMR (150 MHz) δ: 158.12, 136.68, 124.05, 121.64, 75.72, 62.45, 50.85, 30.16, 28.52, 27.90, 27.88, 27.86, 27.82, 27.57, 24.24, 20.82, 11.53. Anal. Calcd for C$_{28}$H$_{54}$Br$_2$N$_2$O.H$_2$O: C, 54.90; H, 9.21; N, 4.57. Found: C, 55.35; H, 9.18; N, 4.58.

Dimethyl-5-tetradecyloxyisophthalate (D9)

The product was generated using general protocol D using dimethyl-5-hydroxyisophthalate (1.037 g, 4.93 mmol), 1-bromotetradecane (1.34 mL, 4.48 mmol), K$_2$CO$_3$ (2.48 g, XXmol), CH$_3$CN (50 mL) yielded 1.21 g (60.2%) of a white solid. $^1$H NMR (CDCl$_3$, 400 MHz) δ: 8.2607 (s, 1H, Ar—H), 7.7396 (s, 2H, Ar—H), 4.0315 (t, 2H, O—CH$_2$, $^3$J=6.62 Hz), 3.9374 (s, 6H, COOCH$_3$), 1.8046 (p, 2H, O—CH$_2$—CH$_2$ $^3$J=6.82 Hz), 1.4660 (p, 2H, O—CH$_2$—CH$_2$—CH$_2$, $^3$J=6.86 Hz), 1.2582 (m, 22H), 0.8809 (t, 3H, CH$_2$—CH$_3$, $^3$J=6.69 Hz 1-Tetradecyloxy-3,5-bis(hydroxymethyl)benzene (E9)

The product was generated using general protocol E using dimethyl-5-tetradecyloxyisophthalate (D9, 1.171 g, 2.88 mmol), lithium aluminum hydride (0.253 g, 6.34 mmol), Et$_2$O (40 mL) yielded 0.538 g (53.3%) of a white solid. $^1$H NMR (CDCl$_3$, 300 MHz) δ: 6.9336 (s, 1H, Ar—H), 6.8501 (s, 2H, Ar—H), 4.6821 (s, 4H, Ar—CH$_2$), 3.9708 (t, 2H, O—CH$_2$, $^3$J=6.58 Hz), 1.7784 (p, 2H, O—CH$_2$—CH$_2$, $^3$J=7.16 Hz), 1.6328 (t, 2H, O—H), 1.4483 (p, 2H, O—CH$_2$—CH$_2$—CH$_2$, $^3$J=7.58 Hz), 1.2625 (m, 20H), 0.8810 (t, 3H, CH$_2$—CH$_3$, $^3$J=6.83 Hz).

1-tetradecyloxy-3,5-bis(bromomethyl)benzene (B9)

The product was generated via general protocol F using 1-tetradecyloxy-3,5-bis(hydroxymethyl)benzene (E9, 2.79 g, 7.95 mmol), PBr$_3$ (1.51 mL, 15.9 mmol), and THF (80 mL). After column chromatography (hexanes, then ramped to 2% EtOAc in hexanes), the reaction yielded 1.26 g (46%) of a white solid. $^1$H NMR (CDCl$_3$, 600 MHz) δ: 6.9819 (s, 1H, Ar—H), 6.8531 (s, 2H, Ar—H), 4.4279 (s, 4H, Ar—CH$_2$), 3.9540 (t, 2H, O—CH$_2$, $^3$J=6.55 Hz), 1.7738 (p, 2H, O—CH$_2$—CH$_2$, $^3$J=7.26 Hz), 1.4474 (p, 2H, O—CH$_2$—CH$_2$—CH$_2$, $^3$J=7.70 Hz), 1.2631 (m, 22H), 0.8809 (t, 3H, CH$_2$—CH$_3$, $^3$J=7.06 Hz).

[(5-tetradecyloxy-m-phenylene)dimethylene]bis[trimethylamonium bromide] (9) (3,5-C14)

The product was generated via general protocol C using 1-tetradecyloxy-3,5-bis(bromomethyl)benzene (B9, 0.888 g, 1.86 mmol), NMe$_3$ (33% wt solution in EtOH, 1.78 mL, 7.46 mmol) and EtOH (20 mL). After recrystallization (EtOH/Et$_2$O) and drying the reaction produced 0.973 g (88.4%) of a white solid, mp=197.2-197.7° C. (dec). $^1$H NMR (MeOD, 400 MHz) δ: 7.4055 (s, 1H, Ar—H), 7.3314 (s, 2H, Ar—H), 4.6073 (s, 4H, Ar—CH$_2$), 4.1045 (t, 2H, O—CH$_2$, $^3$J=6.45 Hz), 3.1796 (s, 18H, N—CH$_3$) 1.8241 (p, 2H, O—CH$_2$—CH$_2$, $^3$J=7.46 Hz), 1.5040 (p, 2H, O—CH$_2$—CH$_2$—CH$_2$, $^3$J=7.39 Hz), 1.2936 (m, 20H), 0.9020 (t, 3H, CH$_2$—CH$_3$, $^3$J=7.04 Hz). Anal. Calcd for C$_{28}$H$_{54}$Br$_2$N$_2$O.H$_2$O: C, 54.90; H, 9.21; N, 4.57. Found: C, 54.96; H, 9.24; N, 4.58.

Dimethyl-5-hexadecyloxyisophthalate (D10)

The product was generated using general protocol D using dimethyl-5-hydroxyisophthalate (3.920 g, 18.7 mmol), 1-bromohexadecane (5.18 g, 17.0 mmol), K$_2$CO$_3$ (9.37 g, 67.8 mmol), CH$_3$CN (100 mL) yielded 6.30 g (86.5%) of a white solid. $^1$H NMR (CDCl3, 600 MHz) δ: 8.26 (t, 3J=1.4 Hz, 1H, Ar—H), 7.74 (d, $_3$J=1.5 Hz, 2H, Ar—H), 4.03 (t, $^3$J=6.5 Hz, 2H, O—CH$_2$), 3.94 (s, 6H, COO—CH$_3$), 1.80 (p, $^3$J=7.3 Hz, 2H, OCH$_2$CH$_2$), 1.46 (p, $^3$J=7.6 Hz, 2H, OCH$_2$CH$_2$CH$_2$), 1.26 (m, 24H), 0.88 (t, $^3$J=6.8, 3H, CH$_2$—CH$_3$.

1-Hexadecyloxy-3,5-bis(hydroxymethyl)benzene (E10)

The product was generated using general protocol E using dimethyl-5-hexadecyloxyisophthalate (D10, 6.30 g), lithium aluminum hydride (1.27 g, 33.5 mmol), Et$_2$O (150 mL) yielded 2.06 g (37.9%) of a white solid. $^1$H NMR (CDCl$_3$, 400 MHz) δ: 6.93 (s, 1H, Ar—H), 6.85 (s, 2H, Ar—H), 4.67 (d, $^3$J=5.9 Hz, 4H, Ar—CH$_2$—OH), 3.97 (t, 6.4 Hz, 2H, O—CH$_2$), 1.78 (p, $^3$J=7.6 Hz, 2H, OCH$_2$CH$_2$), 1.66 (t, $^3$J=6.0 Hz, 2H, CH$_2$—OH), 1.45 (p, $^3$J=7.6 Hz, 2H, O CH$_2$CH$_2$CH$_2$), 1.26 (m, 24H), 0.88 (t, $^3$J=6.6, 3H, CH$_2$—CH$_3$).

1-hexadecyloxy-3,5-bis(bromomethyl)benzene (B10)

The product was generated via general protocol F using 1-hexadecyloxy-3,5-bis(hydroxymethyl)benzene (E10), PBr$_3$, and THF. After column chromatography (hexanes, then ramped to 2% EtOAc in hexanes), the reaction yielded 1.20 g (44%) of a white solid. $^1$H NMR (CDCl$_3$, 400 MHz) δ: (s, 1H, Ar—H), 6.85 (s, 2H, Ar—H), 4.43 (s, 4H, Ar—C$\underline{H}_2$—Br), 3.96 (t, $^3$J=6.4 Hz, 2H, O—C$\underline{H}_2$), 1.77 (p, $^3$J=7.4 Hz, 2H, OCH$_2$C$\underline{H}_2$), 1.45 (p, $^3$J=7.5 Hz, 2H, O CH$_2$CH$_2$C$\underline{H}_2$), 1.26 (m, 24H), 0.88 (t, $^3$J=6.8, 3H, CH$_2$—C$\underline{H}_3$).

1-hexadecyloxy-3,5-bis[(trimethlammonoum bromide)methyl]benzene (10) (3,5-C16)

The product was generated via general protocol C using 1-hexadecyloxy-3,5-bis(bromomethyl)benzene (B10, 1.03 g, 2.04 mmol), NMe$_3$ (33% wt solution in EtOH, 1.95 mL, 8.17 mmol) and EtOH (150 mL). After recrystallization (EtOH/Et$_2$O) and drying the reaction produced 0.723 g (77.2%) of a white solid, mp=208° C. (dec). $^1$H NMR (D$_2$O, 400 MHz) δ: (s, 1H, Ar—H), 7.33 (s, 2H, Ar—H), 4.61 (s, 4H, Ar—C$\underline{H}_2$—N), 4.10 (t, 6.4 Hz, 2H, O—C$\underline{H}_2$), 3.18 (s, 6H, NH$_3$), 1.82 (p, $^3$J=7.4 Hz, 2H, OCH$_2$C$\underline{H}_2$), 1.50 (p, $^3$J=7.6 Hz, 2H, O CH$_2$CH$_2$C$\underline{H}_2$), 1.29 (m, 24H), 0.90 (t, $^3$J=6.6, 3H, CH$_2$—C$\underline{H}_3$). $^{13}$C NMR (CD$_3$OD, 150 MHz) δ: 161.47, 161.52, 130.21, 122.32, 69.91, 69.70, 53.51, 33.07, 30.79, 30.75, 30.74, 30.55, 30.47, 30.33, 27.17, 23.73, 14.44. Anal. Calcd for C$_{30}$H$_{58}$OBr$_2$N$_2$: C, 57.87; H, 9.39; N, 4.50. Found: C, 57.80; H, 9.58; N, 4.49.

A11-A12, B11-B12, 11-12 (MC10, MC14).

Synthetic details and analyses of these compounds have previously been published. [Roszak, K. Z.; Torcivia, S. L.; Hamill, K. M.; Hill, A. R.; Radloff, K. R.; Crizer, D. M.; Middleton, A. M.; Caran, K. L. *J. Colloid Interface Sci.*, 2009, 331, 560-5641.]

Synthesis of Pyridinium Compounds. Menschutkin Reaction:

The 1-hexadecloxy-3,5-bis(bromomethyl)benzene (1 equiv) was suspended in absolute ethanol in a 500 mL 2-neck round bottom flask, which was stirred with a magnetic stir bar under nitrogen. Pyridine (4 equiv, 99%, ACROS) was added with a syringe, and the reaction was refluxed in an oil bath overnight. The flask was then opened, and the excess pyridine and EtOH were allowed to evaporate under the continued flow of N$_2$. The remaining solvent was removed under vacuum, and the crude product was recrystallized from hot EtOH and Et$_2$O.

3,5-C16 (pyridinium)

yielded 0.112 g (66.0%) $^1$H NMR (D$_2$O, $^3$J=6.1 Hz, 400 MHz) d: 9.10 (d, 4H, Pyr-H), 8.63 (t, 2H, $^3$J=7.8 Hz Pyr-H), 8.14 (t, 4H, $^3$J=7.1 Hz Pyr-H), 7.28 (s, 1H, Ar—H), 7.17 (s, 2H, Ar—H), 5.84 (s, 4H, Ar—C$\underline{H}_2$—N), 4.01 (t, 6.4 Hz, 2H, O—C$\underline{H}_2$), 1.76 (p, $^3$J=7.3 Hz, 2H, OCH$_2$C$\underline{H}_2$), 1.45 (p, $^3$J=7.8 Hz, 2H, O CH$_2$CH$_2$C$\underline{H}_2$), 1.29 (m, 24H), 0.90 (t, $^3$J=6.8, 3H, CH$_2$—C$\underline{H}_3$).

Mesitylene-Pyridinium,Pyridinium,Pyridinium [M-P,P,P] (21)

1,3,5-Tribromomethylbenzene (0.1 g, 0.280 mmol) was dissolved in EtOH (5 mL). Pyridine (0.091 mL, 1.12 mmol) was added and the reaction was allowed to run at reflux overnight. Additional pyridine (0.046 mL, 0.56 mmol) was added to and the reaction was allowed to run at reflux overnight once more. Upon concentration of the reaction mixture, the precipitate was stirred in boiling acetone (~10 mL) for five minutes and subsequently filtered hot. After vacuum drying, the reaction produced 0.100 g (60.5%) of 1.

Mesitylene-12,12,12[M-12,12,12] (22)

1,3,5-Tribromomethylbenzene (0.1 g, 0.280 mmol) was dissolved in EtOH (5 mL). N, N-Dimethyldodecylamine (0.250 mL, 0.924 mmol) was added and the reaction was allowed to run at reflux overnight. Upon concentration of the reaction mixture, the precipitate was stirred in acetone (~10 mL) at room temperature for ten minutes. The precipitate was then filtered and vacuum dried.

Mesitylene-14,14,14 [M-14,14,14] (23)

1,3,5-Tribromomethylbenzene (0.1 g, 0.280 mmol) was dissolved in EtOH (5 mL). N, N-Dimethyltetradecylamine (0.280 mL, 0.924 mmol) was added and the reaction was allowed to run at reflux overnight. Upon concentration of the reaction mixture, the precipitate was stirred in acetone (~10 mL) at room temperature for ten minutes. The precipitate was then filtered and vacuum dried. The reaction produced 0.246 g (82.4%).

Mesitylene-16,16,16 [M-16,16,16] (24)

1,3,5-Tribromomethylbenzene (0.1 g, 0.280 mmol) was dissolved in EtOH (5 mL). N, N-Dimethylhexadecylamine (0.311 mL, 0.924 mmol) was added and the reaction was allowed to run at reflux overnight. Upon concentration of the reaction mixture, the precipitate was stirred in acetone (~10 mL) at room temperature for ten minutes. The precipitate was then filtered and vacuum dried. The reaction produced 0.235 g (87.7%).

Intermediate 1 (I1).

1,3,5-Tribromomethylbenzene (1.0 g, 2.8 mmol) was dissolved in acetone (50 mL). Pyridine (0.453 mL, 5.6 mmol) was added and the reaction was allowed to run at room temperature overnight. The reaction precipitate was filtered and subsequently stirred with acetone (~100 mL) for ten minutes. After filtration of the insoluble product, the reaction produced 0.9425 g (77.2%).

Mesitylene-Pyridinium,8,8 [M-P,8,8] (25)

I1 (0.1 g, 0.229 mmol) was dissolved in EtOH (5 mL). N, N-Dimethyloctylamine (0.104 mL, 0.505 mmol) was added and the reaction was allowed to run at reflux for six hours. Upon concentration of the reaction mixture, the precipitate was stirred in acetone (~10 mL) at room temperature for ten minutes. The precipitate was then filtered and dried in vacuo.

Mesitylene-Pyridinium,10,10 [M-P,10,10] (26)

I1 (0.1 g, 0.229 mmol) was dissolved in EtOH (5 mL). N, N-Dimethyldecylamine (0.120 mL, 0.505 mmol) was added and the reaction was allowed to run at reflux for six hours. Upon concentration of the reaction mixture, the precipitate was stirred in acetone (~10 mL) at room temperature for ten minutes. The precipitate was then filtered and dried in vacuo.

Mesitylene-Pyridinium,12,12 [M-P,12,12] (27)

I1 (0.25 g, 0.573 mmol) was dissolved in EtOH (5 mL). N, N-Dimethyldodecylamine (0.341 mL, 1.26 mmol) was added and the reaction was allowed to run at reflux overnight. Upon concentration of the reaction mixture, the precipitate was stirred in acetone (~10 mL) at room temperature for ten minutes. The precipitate was then filtered and dried in vacuo. The reaction produced 0.383 g (77.5%).

Mesitylene-Pyridinium,14,14 [M-P,14,14] (28)

I1 (0.50 g, 1.15 mmol) was dissolved in EtOH (5 mL). N,N-Dimethyltetradecylamine (0.766 mL, 2.52 mmol) was added to the reaction mixture and refluxed overnight. Upon concentration of the reaction mixture, the precipitate was stirred in acetone (~10 mL) at room temperature for ten minutes. The precipitate was then filtered and dried in vacuo. The reaction produced 0.920 g (87.0%).

Mesitylene-Pyridinium,16,16 [M-P,16,16] (29)

I1 (0.25 g, 0.573 mmol) was dissolved in EtOH (5 mL). N,N-Dimethyldodecylamine (0.424 mL, 1.26 mmol) was added to the reaction mixture and refluxed overnight. Upon concentration of the reaction mixture, the precipitate was stirred in acetone (~10 mL) at room temperature for ten minutes. The precipitate was then filtered and dried in vacuo. The reaction produced 0.512 g (91.6%).

ortho-Xylylene-14,14 [oX-14,14] (30)

o-Xylylene dibromide (0.5 g, 1.89 mmol, 1 equiv) was reacted under reflux with N,N-dimethyltetradecylamine (1.15 mL, 3.79 mmol, 2 equiv) in ethanol (10 mL) overnight in 80° C. oil bath. The reaction was taken off the heat and the precipitate was filtered. The crude product was recrystallized from $H_2O$, yielding a white product. $^1H$ NMR (DMSO-d6, 400 MHz) δ: 7.73 (m, 4H, Ar—$\underline{H}$), 4.74 (s, 4H, Ar—C$\underline{H}_2$), 3.39 (m, 4H, N—C$\underline{H}_2$), 2.92 (s, 12H, N—C$\underline{H}_3$), 1.76 (br, 4H, N—CH$_2$—C$\underline{H}_2$), 1.24 (br, 44H, N—CH$_2$—CH$_2$—(C$\underline{H}_2$)$_{11}$, 0.86 (t, 6H, N—(CH$_2$)$_{13}$—C$\underline{H}_3$).

meta-Xylylene-14,14 [mX-14,14] (31)

meta-Xylylene dibromide (0.6 g, 2.3 mmol, 1 equiv) and N,N-dimethyltetradecylamine (2.1 mL, 6.9 mmol, 3 equiv) were combined in dry THF (50 mL). The reaction was run under reflux for 4 h. Upon completion, the reaction was taken off the heat and the crude precipitate was filtered. The product was recrystallized from chloroform/acetone. The recrystallized white solid product was removed by filtration and then dried (1.132 g (65.9%). $^1H$ NMR (CDCl$_3$, 400 MHz) δ: 8.89 (s, 1H, Ar—$\underline{H}$), 7.90 (d, 2H, Ar—$\underline{H}$), 7.51 (t, 1H, Ar—$\underline{H}$), 5.08 (s, 4H, Ar—C$\underline{H}_2$), 3.57 (m, 4H, N—C$\underline{H}_2$), 3.26 (s, 12H, N—CH$_3$), 1.85 (m, 4H, N—CH$_2$—C$\underline{H}_2$), 1.26 (br, 44H, N—CH$_2$—CH$_2$—(CH$_2$)$_{11}$, 0.88 (t, 6H, N—(CH$_2$)$_{13}$—CH$_3$). $^{13}C$ NMR (DMSO-d6, 150 MHz) δ: 138.49, 135.23, 129.83, 128.53, 66.46, 64.94, 49.79, 31.80, 29.58, 29.56, 29.54, 29.53, 29.42, 29.36, 29.24, 29.22, 26.32, 22.91, 22.57, 14.01.

para-Xylylene-14,14[pX-14,14] (32)

para-Xylylene dibromide (0.6 g, 2.3 mmol, 1 equiv) and N,N-dimethyltetradecylamine (2.1 mL, 6.9 mmol, 3 equiv) were combined in dry THF (50 mL). The reaction was run under reflux for 4 h. Upon completion, the reaction was taken off the heat and the crude precipitate was filtered. The product was recrystallized from chloroform/acetone yielding a white solid product.

ortho-Xylylene monopyridinium monobromide (33)

o-xylylene dibromide (15.00 g, 0.05682 mol, 3 equiv), pyridine (1.532 mL, 0.01894 mol, 1 equiv) were dissolved in acetone (100 mL), and the reaction was allowed to run at reflux overnight. The reaction was taken off the heat and the precipitate was removed by filtration and subsequently recrystallized from acetonitrile yielding a white precipitate (4.81 g (74.0%). $^1H$ NMR (DMSO, 400 MHz) δ: 9.18 (d, 2H, Pyr-$\underline{H}$), 8.68 (t, 1H, Pyr-$\underline{H}$), 8.22 (t, 2H, Pyr-$\underline{H}$), 7.59 (s, 1H, Ar—$\underline{H}$), 7.45 (m, 2H, Ar—$\underline{H}$), 7.33 (d, 1H, Ar—$\underline{H}$), 6.17 (s, 2H, Ar—C$\underline{H}_2$), 4.98 (s, 2H, Ar—C$\underline{H}_2$). $^{13}C$ NMR (DMSO, 100 MHz) δ: 146.18, 145.14, 137.20, 132.24, 131.65, 130.47, 130.03, 129.66, 128.34, 59.95, 31.79.

meta-Xylylene monopyridinium monobromide (34)

m-xylylene dibromide (15.00 g, 0.05682 mol, 3 equiv), pyridine (1.532 mL, 0.01894 mol, 1 equiv) were dissolved in acetone (50 mL), and the reaction was allowed to run at reflux overnight. The reaction was taken off the heat and the precipitate was removed by filtration and subsequently recrystallized from acetonitrile yielding a white precipitate (5.15 g, 79.3%). $^1H$ NMR (DMSO, 400 MHz) δ: 9.24 (d, 2H, Pyr-$\underline{H}$), 8.65 (t, 1H, Pyr-$\underline{H}$), 8.21 (t, 2H, Pyr-$\underline{H}$), 7.61 (s, 1H, Ar—$\underline{H}$), 7.47 (m, 3H, Ar—$\underline{H}$), 5.90 (s, 2H, Ar—C$\underline{H}_2$), 4.69 (s, 2H, Ar—CH$_2$). $^{13}C$ NMR (DMSO, 100 MHz) δ: 146.08, 144.87, 139.08, 134.77, 130.21, 129.60, 129.47, 128.72, 128.51, 62.65, 33.68.

ortho-Xylylene-Pyridinium,14 [oX-P,14] (35)

13 (1.00 g, 2.92 mmol, 1 equiv) and N,N-dimethyltetradecylamine (1.062 mL, 3.498 mmol, 1.2 equiv) were dissolved in ethanol (85 mL) and allowed to react under reflux overnight. The reaction was taken off the heat and the precipitate was removed by filtration. The crude product was suspended in acetone for about 20 min. The product was then removed by vacuum filtration, yielding a white solid (0.959 g, 56.3%). $^1H$ NMR (DMSO, 400 MHz) δ: 9.15 (d, 2H, Pyr-$\underline{H}$), 8.70 (t, 1H, Pyr-$\underline{H}$), 8.23 (t, 2H, Pyr-$\underline{H}$), 7.74 (m, 1H, Ar—$\underline{H}$), 7.57 (m, 2H, Ar—$\underline{H}$), 7.25 (m, 1H, Ar—$\underline{H}$), 6.31 (s, 2H, Ar—C$\underline{H}_3$), 4.92 (s, 2H, Ar—C$\underline{H}_3$), 3.49 (m, 2H, N—C$\underline{H}_2$), 3.03 (s, 6H, N—CH$_3$), 1.81 (m, 3H, N—CH$_2$—C$\underline{H}_2$), 1.25 (br, 22H, N—CH$_2$—CH$_2$—(CH$_2$)$_{11}$), 0.85 (t, N—CH$_2$—CH$_2$—(CH$_2$)$_{11}$—C$\underline{H}_3$).

meta-Xylylene-Pyridinium,14 [mX-P,14] (36)

13 (0.622 g, 1.81 mmol, 1 equiv) and N,N-dimethyltetradecylamine (0.66 mL, 2.2 mmol, 1.2 equiv) were dissolved in ethanol (85 mL) and allowed to react under reflux overnight. The reaction was taken off the heat and the precipitate was removed by filtration. The crude product was recrystallized from acetone, yielding a white solid (0.728 g, 68.7%).

1-tetradecyloxy-2,5-bis(4,4'-bipyridinium)benzene, bis-bromide salt (41)

1-tetradecyloxy-2,5-dimethylbenzene 1-bromotetradecane (44.4 mL, 0.149 mol), 2,5-dimethylphenol (20.0 g, 0.164 mol) and K$_2$CO$_3$ (82.4 g, 0.596 mol) were combined in a round bottom flask in acetonitrile (200 mL). The flask was equipped with a stir-bar, and a water-cooled condenser and protected under a nitrogen atmosphere. The mixture was heated at reflux for overnight. Synthetic progress was monitored by the disappearance of the signal (triplet) from the C1 hydrogens on the alkyl bromide (~3.5 ppm) in $^1$H NMR. Upon completion, the reaction was removed from heat and excess $K_2CO_3$ was removed by gravity filtration (rinsed with $CH_2Cl_2$). The crude product was concentrated in vacuo and the resulting material was dissolved in $CH_2Cl_2$, washed with 1 M NaOH (2×, to remove unreacted 2,5-dimethylphenol or p-cresol), $dH_2O$ (2×) and brine (1×), dried over $Na_2SO_4$, gravity filtered, and concentrated in vacuo to remove the solvent. The material was of sufficient purity (by $^1$H and $^{13}$C NMR) to be used in the subsequent reactions. Yielded 41.0 g (86%) of an off-white solid, mp=36.9-37.9° C. $^1$H NMR ($CDCl_3$, 400 MHz) δ: 7.01 (d, $^3$J=7.4 Hz, 1H, Ar—H); 6.66 (d, $^3$J=7.6 Hz, 1H, Ar—H); 6.65 (s, 1H, Ar—H); 3.95 (t, $^3$J=6.5 Hz, 2H, $OCH_2$); 2.33 (s, 3H); 2.20 (s, 3H); 1.80 (m, 2H, $OCH_2CH_2$); 1.49 (m, 2H, $OCH_2CH_2CH_2$); 1.42-1.26 (m, 20H); 0.90 (t, $^3$J=6.8 Hz, 3H, $CH_2CH_3$). $^{13}$C NMR ($CDCl_3$, 100 MHz) δ: 157.15, 136.40, 130.25, 123.65, 120.53, 112.01, 67.88, 31.93, 29.70, 29.68, 29,66, 29.62, 29.42, 29.40, 29.37, 26.16, 22.70, 21.40, 15.78, 14.11. HRMS (DART): [M+H]$^+$=319.29460 (calcd for $C_{22}H_{39}O$ 319.29954).

1-tetradecyloxy-2,5-bis(bromomethyl)benzene

All glassware was dried in an oven overnight and flushed with $N_2$ (g) prior to use. A solution of 1-tetradecyloxy-2,5-dimethylbenzene (A14, 15.0 g, 47.1 mmol) in carbon tetrachloride (510 mL) was prepared in a round bottom flask equipped with a water-cooled condenser, magnetic stir bar and protected with under a nitrogen atmosphere. N-bromosuccinimide (99%, 16.9 g, 94.2 mmol), benzoyl peroxide (0.234 g, 0.942 mmol) were added and the reaction was run at room temperature under irradiation from a 300 W/82V tungsten halogen lamp. The product was generated via general protocol B using, and $CCl_4$ (510 mL). The reaction was run in 6 equal batches at room temperature under irradiation for 30-60 min per batch. Reaction progress was monitored by the disappearance of the insoluble NBS at the bottom of the flask and the appearance of the lower density insoluble succinimide byproduct that floated to the surface of the reaction mixture. After filtration of the succinimide, the solvent was removed in vacuo. After two recrystallizations of the combined crude product from n-hexane, 5.21 g (23%) of the pure product was obtained as a white solid, mp=64.0-64.2° C. $^1$H NMR ($CDCl_3$, 600 MHz) δ: 7.28 (d, $^3$J=7.6 Hz, 1H, Ar—H); 6.92 (dd, $^3$J=7.6 Hz, $^4$J=1.6 Hz, 1H, Ar—H); 6.88 (d, $^4$J=1.6 Hz, 1H, Ar—H); 4.54 (s, 2H); 4.45 (s, 2H); 4.04 (t, $^3$J=6.4 Hz, 2H, $OCH_2$); 1.84 (m, 2H, $OCH_2CH_2$); 1.51 (m, 2H, $OCH_2CH_2CH_2$); 1.40-1.21 (m, 20H); 0.88 (t, $^3$J=7.0 Hz, 3H, $CH_2CH_3$). $^{13}$C NMR ($CDCl_3$ 150 MHz) δ: 157.11, 139.73, 131.02, 126.50, 120.92, 112.27, 68.31, 33.36, 31.92, 29.68, 29.67, 29.65, 29.59, 29.58, 29.36, 29.33, 29.15, 28.48, 26.06, 22.69, 14.13. HRMS (DART): [M–Br]$^{3O}$=395.19344 (calcd for $C_{22}H_{36}BrO$ 395.19440).

1-tetradecyloxy-2,5-bis(4,4'-bipyridinium)benzene, bis-bromide salt 4,4'bipyridine (98.9 mg, 0.634 mmol) was dissolved in $CH_3CN$ (10 mL) and brought to reflux in a round bottom flask equipped with a nitrogen-protected, water-cooled reflux condenser. A solution of 1-tetradecyloxy-2,5-bis(bromomethyl) benzene (100 mg, 0.210 mmol) dissolved in $CH_3CN$ (2.5 mL) and $CHCl_3$ (5.0 mL) was added dropwise to the solution of 4,4'-bipyridine. The reflux condenser was switched out for a distillation head and condenser ~1 h in order to distill off the $CHCl_3$. After this, the reflux condenser was switched back in and the reaction was allowed to run at reflux for 5 h. Upon cooling, the solid product precipitated from solution. It was collected by filtration and washed with cold $CH_3CN$, and subsequently recrystallized from $CH_3CN$ and dried, producing a yellow crystalline product (128 mg, 0.162 mmol, 77%). $^1$NMR ($CD_3OD$, 400 MHz) δ: 9.22 (d, $^3$J=6.4 Hz, 2H, Ar—H); 9.10 (d, $^3$J=6.4 Hz, 2H, Ar—H); 8.82 (m, 4H, Ar—H), 8.53 (m, 4H, Ar—H); 7.97 (m, 4H, Ar—H); 7.74 (d, $^3$J=7.4 Hz, 1H, Ar—H); 7.38 (s, 1H, Ar—H); 7.28 (d, 7.4 Hz, 1H, Ar—H); 5.93 (s, 2H, Ar—$CH_2$—N); 5.89 (s, 2H, Ar—$CH_2$—N); 4.09 (t, 2H, $^3$J=6.4 Hz, $OCH_2$); 1.73 (m, 2H, $OCH_2CH_2$); 1.35-1.13 (m, 22H), 0.89 (t, 6.6 Hz, $CH_2CH_3$).

What is claimed is:

1. A pharmaceutical composition comprising a compound of formula I:

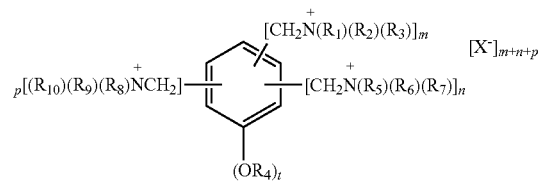

wherein

R$_1$, R$_2$, and R$_3$, and/or R$_5$, R$_6$, and R$_7$, and/or R$_8$, R$_9$, and R$_{10}$, together with the nitrogen atom to which they are attached, form a pyridinium or pyridyl-substituted pyridinium;

m is 1;

n is 1;

p is 0;

t is 1;

R$_4$ is C$_{8-22}$alkyl; and

X is halogen or tartrate;

and a pharmaceutically acceptable carrier or diluent.

2. The pharmaceutical composition of claim 1, wherein the compound of formula I is one of

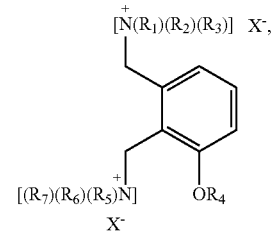

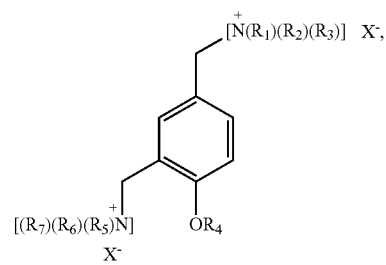

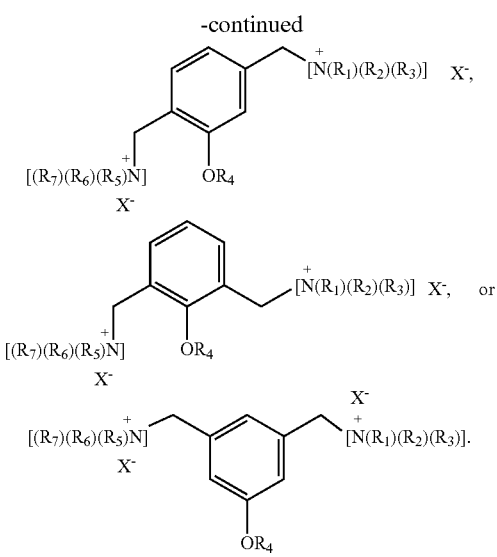

3. The pharmaceutical composition of claim 1, wherein the compound of formula I is

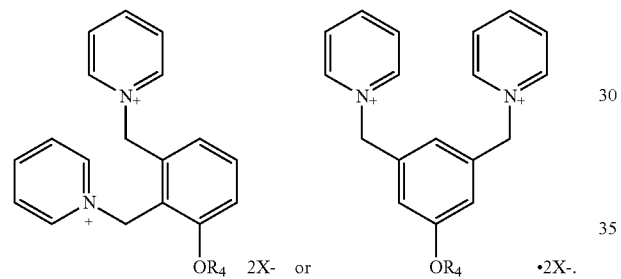

4. The pharmaceutical composition of claim 1, wherein $R_4$ is —$C_{10-18}$alkyl.

5. The pharmaceutical composition of claim 4, wherein $R_4$ is —$C_{10}H_{21}$.

6. The pharmaceutical composition of claim 4, wherein $R_4$ is —$C_{12}H_{25}$.

7. The pharmaceutical composition of claim 4, wherein $R_4$ is —$C_{14}H_{29}$.

8. The pharmaceutical composition of claim 4, wherein $R_4$ is —$C_{16}H_{33}$.

9. The pharmaceutical composition of claim 4, wherein $R_4$ is —$C_{18}H_{37}$.

10. The pharmaceutical composition of claim 1, wherein the compound of formula I is selected from the following Table:

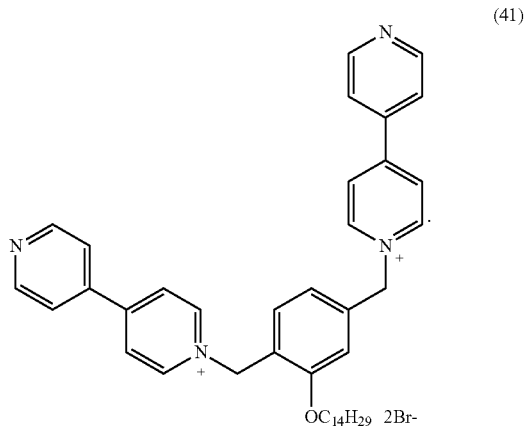

| Comp. No. | Substitution | $R_4$ |
|---|---|---|
| 15 | 2, 3 | —$C_{14}H_{29}$ |
| 40 | 3, 5 | —$C_{14}H_{29}$ |
| 16 | 3, 5 | —$C_{16}H_{33}$. |

11. The pharmaceutical composition of claim 1, wherein the compound of formula I is (41)

12. The pharmaceutical composition of claim 1, wherein X is Br.

* * * * *